United States Patent
Van Der Wall et al.

(10) Patent No.: US 11,813,069 B2
(45) Date of Patent: Nov. 14, 2023

(54) DIAGNOSING REFLUX DISEASE

(71) Applicant: GORR PTY LIMITED, Meadowbank (AU)

(72) Inventors: Hans Van Der Wall, Meadowbank (AU); Gregory L. Falk, Meadowbank (AU)

(73) Assignee: GORR PTY LIMITED, Meadowbank (AU)

( * ) Notice: Subject to any disclaimer, the term of this patent is extended or adjusted under 35 U.S.C. 154(b) by 895 days.

(21) Appl. No.: 16/499,687

(22) PCT Filed: Mar. 29, 2018

(86) PCT No.: PCT/AU2018/050301
§ 371 (c)(1),
(2) Date: Sep. 30, 2019

(87) PCT Pub. No.: WO2018/176105
PCT Pub. Date: Oct. 4, 2018

(65) Prior Publication Data
US 2020/0037948 A1    Feb. 6, 2020

(30) Foreign Application Priority Data
Mar. 31, 2017   (AU) ................. 2017202137

(51) Int. Cl.
*A61B 5/00*    (2006.01)
*A61B 6/03*    (2006.01)
(Continued)

(52) U.S. Cl.
CPC ............ *A61B 5/4211* (2013.01); *A61B 5/004* (2013.01); *A61B 5/0071* (2013.01); *A61B 6/032* (2013.01);
(Continued)

(58) Field of Classification Search
CPC ..... A61B 5/4211; A61B 5/004; A61B 5/0071; A61B 6/032; A61B 6/037; A61B 6/487;
(Continued)

(56) References Cited

U.S. PATENT DOCUMENTS

2007/0203401 A1*  8/2007  Gordon .................. G16H 50/70
                                                            600/300

OTHER PUBLICATIONS

Lim, Hyun Chul et al. "Effects of the Addition of Mosapride to Gastroesophageal Reflux Disease Patients on Proton Pump Inhibitor: A Prospective Randomized, Double-blind Study." Journal of neurogastroenterology and motility vol. 19,4 (2013): 495. (Year: 2013).*

(Continued)

*Primary Examiner* — Angela M Hoffa
*Assistant Examiner* — Younhee Choi
(74) *Attorney, Agent, or Firm* — LEWIS ROCA ROTHGERBER CHRISTIE LLP

(57) ABSTRACT

A method (100) and system (1) for diagnosing reflux disease in an individual (3). The method (100) comprises: administering (110) an oral dose (17) of tracer in to the individual; capturing (120), with a single photon emission computed tomography (SPECT) scanner (5), data representative of multiple image frames (21) of the individual in areas of interest (23) that include the pharynx (25) and oesophagus (27), wherein the data representative of multiple image frames (21) are captured over time after administration of the oral dose; and determining (130) one or more trend(s) in tracer activity over time in the areas of interest (23) based on the data representative of multiple image frames (21), wherein the trend(s) in tracer activity over time is indicative of a reflux disease.

18 Claims, 27 Drawing Sheets

(51) Int. Cl.
*A61B 6/00* (2006.01)
*A61B 5/1455* (2006.01)
(52) U.S. Cl.
CPC .............. *A61B 6/037* (2013.01); *A61B 6/487* (2013.01); *A61B 6/5217* (2013.01); *A61B 5/14551* (2013.01); *A61B 6/463* (2013.01)
(58) Field of Classification Search
CPC ... A61B 6/5217; A61B 5/14551; A61B 6/463; A61B 6/5235; A61B 6/486; A61B 5/0035; A61B 6/50; G01T 1/164; G16H 50/30
See application file for complete search history.

(56) References Cited

OTHER PUBLICATIONS

Williams, P J, and P M Bailey. "Comparison of the reinforced laryngeal mask airway and tracheal intubation for adenotonsillectomy." British journal of anaesthesia vol. 70,1 (1993): 30 (Year: 1993).*

Tatsch, K et al. "Reappraisal of quantitative esophageal scintigraphy by optimizing results with ROC analyses."Journal of nuclear medicine : official publication, Society of Nuclear Medicine vol. 37,11 (1996): 1799 (Year: 1996).*

Mariani, Giuliano et al. "Radionuclide gastroesophageal motor studies."Journal of nuclear medicine : official publication, Society of Nuclear Medicine vol. 45,6 (2004): 1004 (Year: 2004).*

Warrington, James Claude, and Martin Charron. "Pediatric gastrointestinal nuclear medicine." Seminars in nuclear medicine vol. 37,4 (2007): 269 (Year: 2007).*

Andrews, Thomas M, and Nicklas Orobello. "Histologic versus pH probe results in pediatric laryngopharyngeal reflux." International journal of pediatric otorhinolaryngology vol. 77,5 (2013): 813 (Year: 2013).*

Falk, Gregory L et al. "Scintigraphy in laryngopharyngeal and gastroesophageal reflux disease: a definitive diagnostic test?." World journal of gastroenterology vol. 21,12 (2015): 3619. (Year: 2015).*

Steingoetter, Andreas et al. "Volume distribution and acidity of gastric secretion on and off proton pump inhibitor treatment: a randomized double-blind controlled study in patients with gastro-esophageal reflux disease (GERD) and healthy subjects." BMC gastroenterology vol. 15 111. Sep. 2, 2015,1 (Year: 2015).*

Hou, Peng et al. "Detection of salivary aspiration using radionuclide salivagram SPECT/CT in patients with COPD exacerbation: a preliminary study." Journal of thoracic disease vol. 8,10 (2016): 2730 (Year: 2016).*

Search Report of corresponding PCT/AU2018/050301, dated Jun. 18, 2018, 4 pages.

Written Opinion of corresponding PCT/AU2018/050301, dated Jun. 18, 2018, 5 pages.

Falk, et al., "Scintigraphy in laryngopharyngeal and gastroesophageal reflux disease: A definitive diagnostic test?," World J Gastroenterology, vol. 21, Issue 12, Mar. 28, 2015, pp. 3619-3627.

Mariani, et al., "Radionuclide Gastroesophageal Motor Studies," J Nucl Med., vol. 45, No. 6, Jun. 2004, pp. 1004-1028.

Hou, et al., "Detection of salivary aspiration using radionuclide salivagram SPECT/CT in patients with COPD exacerbation: a preliminary study," J Thorac Dis 2016; 8 (10): pp. 2730-2737.

Puranik, et al., "Scintigraphic scoring system for grading severity of gastro-esophageal reflux on 99mTc sulfur colloid gastro-esophageal reflux scintigraphy: A prospective study of 39 cases with pre and post treatment assessment," Indian Journal of Nuclear Medicine, vol. 28, Issue 2, Apr.-Jun. 2013, pp. 79-84.

Warrington et al: "Pediatric Gastrointestinal Nuclear Medicine," Seminars in Nuclear Medicine, Elsevier, Amsterdam, NL, vol. 37, No. 4, Jul. 1, 2007 (Jul. 1, 2007), pp. 269-285, XP022096265, ISSN: 0001-2998, DOI:10.1053/J.SEMNUCLMED.2007.02.005.

GE Healthcare: "GoldSeal Infinia Hawkeye 4," Jan. 1, 2016 (Jan. 1, 2016), XP055748300, Retrieved from the Internet: URL:https://www.gehealthcare.com/-/jssmedia/7d3e4b30c5284eba8f42eb5ac27372e2.pdf [retrieved on Nov. 9, 2020].

Extended European Search Report dated Nov. 17, 2020 for European counterpart Application No. 18775753.9 (9 pages).

* cited by examiner

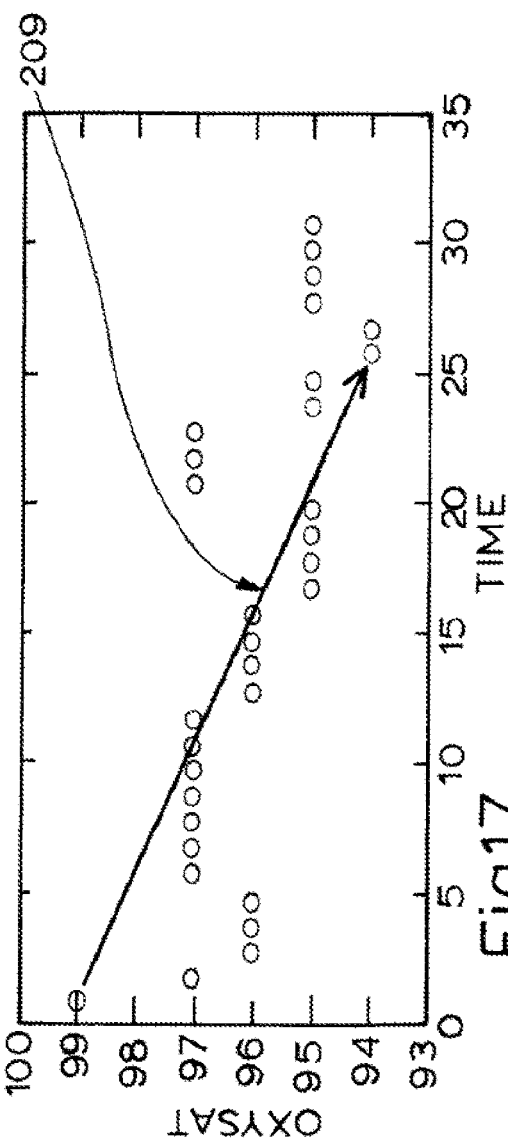

DIAGNOSING REFLUX DISEASE

CROSS-REFERENCE TO RELATED APPLICATION(S)

This application is a National Phase Patent Application and claims priority to and the benefit of International Application Number PCT/AU2018/050301, filed on Mar. 29, 2018, which claims priority to Australian Patent Application Number 2017202137, filed on Mar. 31, 2017, the entire contents of all of which are incorporated herein by reference.

TECHNICAL FIELD

The present disclosure provides a method and system for diagnosing reflux disease in an individual. The present disclosure includes a method and system that uses scintigraphy for diagnosis.

BACKGROUND

Gastroesophageal reflux is a common condition that may occur on a physiological basis in large portions of a population. However, a major medical issue is determining and separating such physiological reflux from pathological reflux such as gastro oesophageal reflux disease (GORD) (also known as gastroesophageal reflux disease, (GERD)). Symptomatic forms of GORD are prevalent. However of greater concern is that approximately 30% of people with pathological reflux are asymptomatic.

Gastric acids may cause significant tissue injury to relatively unprotected sites such as the oesophagus and laryngopharynx. The complications of reflux may be divided into proximal and distal. Distal complications (that are towards the oesophagus) include: metaplasia of the oesophageal lining in the lower oesophagus; and Barrett's oesophagus with the subsequent increased risk of carcinoma of the oesophagus. Proximal complications (closer to the pharynx) include: laryngopharyngeal reflux (LPR) with a heightened risk of carcinoma of the pharynx, lung aspiration and contamination of the sinuses and middle ear with the risk of chronic infection.

The area above the pharynx is generally out of reach of standard diagnostic techniques using pH, impedance and manometric monitoring. Endoscopy of the oesophagus and indirect laryngoscopy are said to yield a diagnosis in less than 50% of cases. Therefore there are difficulties in diagnosing GORD, the severity and effects.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

The present disclosure includes diagnosing reflux disease in an individual by observing tracer activity, from an oral dose of tracer, in an area above the stomach of the individual. Trends in tracer activity over time may be indicative of reflux disease.

There is provided a method for diagnosing reflux disease in an individual, the method comprising:

(A) administering an oral dose of tracer in 75 mL to 200 mL of water to the individual;

(B) capturing, with a single photon emission computed tomography (SPECT) scanner, data representative of multiple image frames of the individual in areas of interest that include the pharynx and oesophagus, wherein the data representative of multiple image frames are captured over time after administration of the oral dose; and (C) determining one or more trend(s) in tracer activity over time in the areas of interest based on the data representative of multiple image frames, wherein each image frame has a sampling time of greater than 5 seconds and less than or equal to 60 seconds, wherein the trend(s) in tracer activity over time is indicative of reflux disease.

In some examples of the method, the tracer includes technetium phytates in the range of 60 to 100 MBq.

In some examples of the method, the individual is administered an oral dose of Proton Pump Inhibitors (PPI) before the administration of the oral dose of tracer. The oral dose of PPI may be administered between 30 to 90 minutes before administering the oral dose of tracer.

In some examples, the method further comprises determining a frequency of the trend in tracer activity in the pharynx that is above a specified threshold or in a specified range, wherein a higher frequency is indicative of intermittent laryngopharyngeal reflux and a lower frequency, or single occurrence, is indicative of continuous laryngopharyngeal reflux. A frequency indicative of intermediate laryngopharyngeal reflux may be indicative of an increased probability of lung aspiration of refluxate.

In some example, the method further comprises capturing, with an oxygen saturation sensor, an oxygen saturation of the blood of the individual over time, wherein a decreasing trend in oxygen saturation and an indication of intermittent laryngopharyngeal reflux is indicative of a reflex mediated laryngopharyngeal spasm.

The method may further comprise determining an amplitude and/or time of the trend in tracer activity in the pharynx that is above a second specified threshold, wherein the amplitude and/or time is indicative of a severity of laryngopharyngeal reflux.

In some examples of the method, the tracer includes technetium diethylenetriaminepentacetate (99mTcDTPA) in the range of 40 to 100 MBq.

In some examples of the method, an ascending or flat trend in tracer activity over time in the oesophagus is indicative of the tracer in the oesophagus and significant gastroesophageal reflux.

In some examples of the method, an ascending-trend in tracer activity over time in the pharynx is indicative of laryngopharyngeal reflux.

In some examples of the method, after administering an oral dose of 99mTcDTPA, the method further includes administering 50 to 75 mL of water.

In some examples of the method, at least part of the data representative of multiple image frames are captured over a first time period that is up to between 5 and 30 minutes after administration of the oral dose and with the individual in the upright position.

In some examples of the method, at least part of the data representative of multiple image frames is captured over a second time period that occurs up to 30 minutes after administration of the oral dose and with the individual in the supine position.

In some examples of the method, at least part of the data representative of multiple image frames are captured over a third time period that occurs between 90 minutes to 150 minutes after administration of the oral dose and with the individual in the supine position.

In some examples of the method, the sampling time for each image frame is in the range of 15 to 30 seconds.

In some examples of the method, the oral dose of tracer is in the range of 40 to 60 MBq in approximately 150 mL of water.

In some examples of the method, the area of interest that includes the oesophagus includes the upper oesophagus and the lower oesophagus.

In some examples of the method, the areas of interest includes the stomach of the individual and the method further comprises:
  determining a trend in tracer activity by exponential fit of tracer activity in the stomach over time; and
  determining a time to half clearance of gastric liquid based on the exponential fit of tracer activity,
    wherein a time to half clearance greater than 16 minutes is indicative of an individual as having a prolonged liquid gastric emptying.

In some examples, the method further includes capturing, with the SPECT scanner, data representative of image frames of a background area, wherein the background area is outside a fluid path of the nasopharynx, larynx, and oesophagus.

In some examples of the method, the SPECT scanner is a SPECT/CT scanner that further includes x-ray computed tomography (CT) to provide data representative of multiple image frames of the individual that includes details of anatomical features of the individual.

In some examples of the method, the areas of interest include nasal turbinates, the maxillary sinuses, Eustachian tube and/or the middle ears.

In some examples of the method, determining the trend in tracer activity over time in the areas of interest includes linear regression of tracer activity over time in one or more areas of interest.

There is also provided a system for diagnosing reflux disease in an individual, wherein the individual is administered an oral dose of tracer in 75 mL to 200 mL of water, the system comprising:
  a single photon emission computed tomography and x-ray computed tomography (SPECT/CT) scanner to capture data representative of multiple image frames of the individual in areas of interest that include the pharynx and oesophagus, wherein the data representative of multiple image frames are captured over time after administration of the oral dose;
  a processing device configured to:
    determine one or more trend(s) in tracer activity over time in the areas of interest based on the multiple image frames of the individual in the areas of interest over time, wherein each image frame has a sampling time of greater than 5 seconds and less than or equal to 60 seconds, wherein the trend(s) in tracer activity over time is indicative of reflux disease.

In some examples of the system, the tracer includes technetium phytates in the range of 60 to 100 MBq.

In some examples of the system, the processing device is further configured to:
    determine a frequency of the trend in tracer activity in the pharynx that is above a specified threshold or in a specified range, wherein a higher frequency is indicative of intermittent laryngopharyngeal reflux and a lower frequency, or single occurrence, is indicative of continuous laryngopharyngeal reflux. A frequency indicative of intermediate laryngopharyngeal reflux may be indicative of an increased probability of lung aspiration of refluxate.

In some examples, the system further comprises:
  an oxygen saturation sensor to capture an oxygen saturation of the blood of the individual over time,
  wherein a decreasing trend in oxygen saturation and an indication of intermittent laryngopharyngeal reflux is indicative of a reflex mediated laryngopharyngeal spasm.

In some examples of the system, the processing device is further configured to determine an amplitude and/or time of the trend in tracer activity in the pharynx that is above a second specified threshold, wherein the amplitude and/or time is indicative of a severity of laryngopharyngeal reflux.

In some examples of the system, the tracer includes technetium diethylenetriaminepentacetate (99mTcDTPA) in the range of 40 to 100 MBq.

In some examples of the system, the processing device is further configured to:
  determine, separately, the tracer activity in each of the areas of interest including the pharynx and the oesophagus; and
  determine, for each area of interest, the trend in tracer activity by linear regression of tracer activity over time.

In some examples of the system, an ascending or flat trend in tracer activity over time in the oesophagus is indicative of the tracer in the oesophagus and significant gastroesophageal reflux.

In some examples of the system, an ascending trend in tracer activity over time in the pharynx is indicative of aspiration of the tracer and laryngopharyngeal reflux.

In some examples of the system, at least part of the data representative of multiple image frames are captured over a first time period that is up to between 5 and 30 minutes after administration of the oral dose and with the individual in the upright position.

In some examples of the system, at least part of the data representative of multiple image frames are captured over a second time period that occurs up to 30 minutes after administration of the oral dose and with the individual in the supine position.

In some examples of the system, at least part of the data representative of multiple image frames are captured over a third time period that occurs between 90 minutes to 150 minutes after administration of the oral dose and with the individual in the supine position.

In some examples of the system, the sampling time is in the range of 15 to 30 seconds.

In some examples of the system, the processing device is further configured to:
  determine, separately, the tracer activity in the upper oesophagus and the lower oesophagus; and
  determine, for the upper oesophagus and the lower oesophagus, the respective trend in tracer activity by least squares fit or linear regression of tracer activity over time.

In some examples of the system, the areas of interest includes the stomach of the individual and the processing device is further configured to:
  determine the tracer activity in the stomach;

determine, for the stomach, the trend in tracer activity by exponential fit of tracer activity over time; and determine a time to half clearance of gastric liquid based on the exponential fit of tracer activity, wherein a time to half clearance greater than 16 minutes is indicative of an individual as having prolonged liquid gastric emptying.

In some examples of the system, the processing device is further configured to:

identify, from the data representative of multiple image frames, one or more sub-regions that correspond to the pharynx, upper oesophagus, lower oesophagus and the stomach.

In some examples of the system, the SPECT scanner further captures data representative of image frames of a background area, wherein the background area is outside a fluid path of the nasopharynx, larynx, and oesophagus, wherein the processing device is further configured to:

determine background radiation based on activity in the background area; and enhance the data representative of the multiple images by factoring the background radiation.

In some examples of the system, the SPECT scanner is a SPECT/CT scanner that further includes x-ray computed tomography (CT) to provide data representative of multiple image frames of the individual that includes details of anatomical features of the individual.

In some examples of the system, the areas of interest includes the nasal turbinates, maxillary sinuses, Eustachian tube and/or the middle ears, wherein the processing device is further configured to:

generate, at a display, one or more representations of the tracer activity at the nasal turbinates, maxillary sinuses, Eustachian tube and/or the middle ears, wherein the tracer activity at the nasal turbinates, maxillary sinuses, Eustachian tube and/or middle ears is indicative of aspiration of the tracer.

In some examples of the system, the processing device is further configured to:

generate, at a display, one or more representations of the one or more trend(s) in tracer activity over time.

A computer-implemented method for diagnosing reflux disease in an individual, wherein the individual is administered an oral dose of tracer in 75 mL to 200 mL of water, the method comprising:

receiving, from a single photon emission computed tomography (SPECT) scanner, data representative of multiple image frames of the individual in areas of interest that include the pharynx and oesophagus, wherein the data representative of multiple image frames are captured over time after administration of the oral dose;

determining one or more trend(s) in tracer activity over time in the areas of interest based on the multiple images of the individual over time, wherein each image frame has a sampling time of greater than 5 seconds and less than or equal to 60 seconds, wherein the trend(s) in tracer activity over time is indicative of a reflux disease.

determining if refluxate has been aspirated into the lungs in the delayed study and semi-quantitating this by a line-profile analysis.

The tracer may include technetium phytates in the range of 60 to 100 MBq.

The computer-implemented method may further comprise determining a frequency of the trend in tracer activity in the pharynx that is above a specified threshold or in a specified range, wherein a higher frequency is indicative of intermittent laryngopharyngeal reflux and a lower frequency, or single occurrence, is indicative of continuous laryngopharyngeal reflux. A frequency indicative of intermediate laryngopharyngeal reflux may be indicative of an increased probability of lung aspiration of refluxate.

The computer-implemented method may further comprise capturing, with an oxygen saturation sensor, an oxygen saturation of the blood of the individual over time, wherein a decreasing trend in oxygen saturation and an indication of intermittent laryngopharyngeal reflux is indicative of a reflex mediated laryngopharyngeal spasm.

The computer-implemented method may further comprise determining an amplitude and/or time of the trend in tracer activity in the pharynx that is above a second specified threshold, wherein the amplitude and/or time is indicative of a severity of laryngopharyngeal reflux.

In some examples of the method, the tracer includes technetium diethylenetriaminepentacetate (99mTcDTPA) in the range of 40 to 100 MBq.

In some examples, the computer-implemented method further comprises:

determining, separately, the tracer activity in each of the areas of interest including the pharynx and the oesophagus; and determining, for each area of interest, the trend in tracer activity by linear regression of tracer activity over time.

In some examples of the computer-implemented method, an ascending or flat trend in tracer activity over time in the oesophagus is indicative of the tracer in the oesophagus significant gastroesophageal reflux.

In some examples of the computer-implemented method, an ascending trend in tracer activity over time in the pharynx is indicative of aspiration of the tracer and laryngopharyngeal reflux.

In some examples of the computer-implemented method, at least part of the data representative of multiple image frames are captured over a first time period that is up to between 5 and 30 minutes after administration of the oral dose and with the individual in the upright position.

In some examples of the computer-implemented method, at least part of the data representative of multiple image frames are captured over a second time period that occurs up to 30 minutes after administration of the oral dose and with the individual in the supine position.

In some examples of the computer-implemented method, at least part of the data representative of multiple image frames are captured over a third time period that occurs between 90 minutes to 150 minutes after administration of the oral dose and with the individual in the supine position.

In some examples of the computer-implemented method, the sampling time is in the range of 15 to 30 seconds.

In some examples, the computer-implemented method further comprises:

determining, separately, the tracer activity in the upper oesophagus and the lower oesophagus; and determining, for the upper oesophagus and the lower oesophagus, the respective trend in tracer activity by linear regression of tracer activity over time.

In some examples, the areas of interest includes the stomach of the individual and the computer-implemented method further comprises:

determining the tracer activity in the stomach;

determining, for the stomach, the trend in tracer activity by exponential fit of tracer activity over time; and determining a time to half clearance of gastric liquid based on the exponential fit of tracer activity, wherein a time to half clearance greater than 16 minutes is indicative of an individual as having prolonged liquid gastric emptying.

In some examples, the computer-implemented method further comprises:
identifying, from the data representative of multiple image frames, one or more sub-regions that correspond to the pharynx, upper oesophagus, lower oesophagus and the stomach.

In some examples the method comprises receiving data representative of image frames of a background area, wherein the background area is outside a fluid path of the nasopharynx, larynx, and oesophagus, wherein the method further comprises:
determining background radiation based on activity in the background area; and
enhancing the data representative of the multiple images by factoring the background radiation.

In some examples the SPECT scanner is a SPECT/CT scanner that further includes x-ray computed tomography (CT), wherein the computer-implemented method further includes receiving, from the SPECT/CT scanner, data representative of multiple image frames of the individual that includes details of anatomical features of the individual.

In some examples the areas of interest includes the nasal turbinates, maxillary sinuses, Eustachian tube and/or the middle ears, and the computer-implemented method further comprises:
generating, at a display, one or more representations of the tracer activity at the nasal turbinates, maxillary sinuses, Eustachian tube and/or the middle ears,
wherein the tracer activity at the nasal turbinates, maxillary sinuses, Eustachian tube and/or middle ears is indicative of aspiration of the tracer.

In some examples the method further comprises:
generating, at a display, one or more representations of the one or more trend(s) in tracer activity over time.

Software that, when executed by a computer, causes the computer to perform the method described above.

BRIEF DESCRIPTION OF DRAWINGS

Examples of the present disclosure will be described with reference to the figures below:

FIG. 17 shows graphical representation data including a graph illustrating tracer activity in the pharynx that indicates frequency of laryngopharyngeal reflux and a graph showing a decrease in oxygen saturation;

DESCRIPTION OF EMBODIMENTS

Overview

Figure 1:
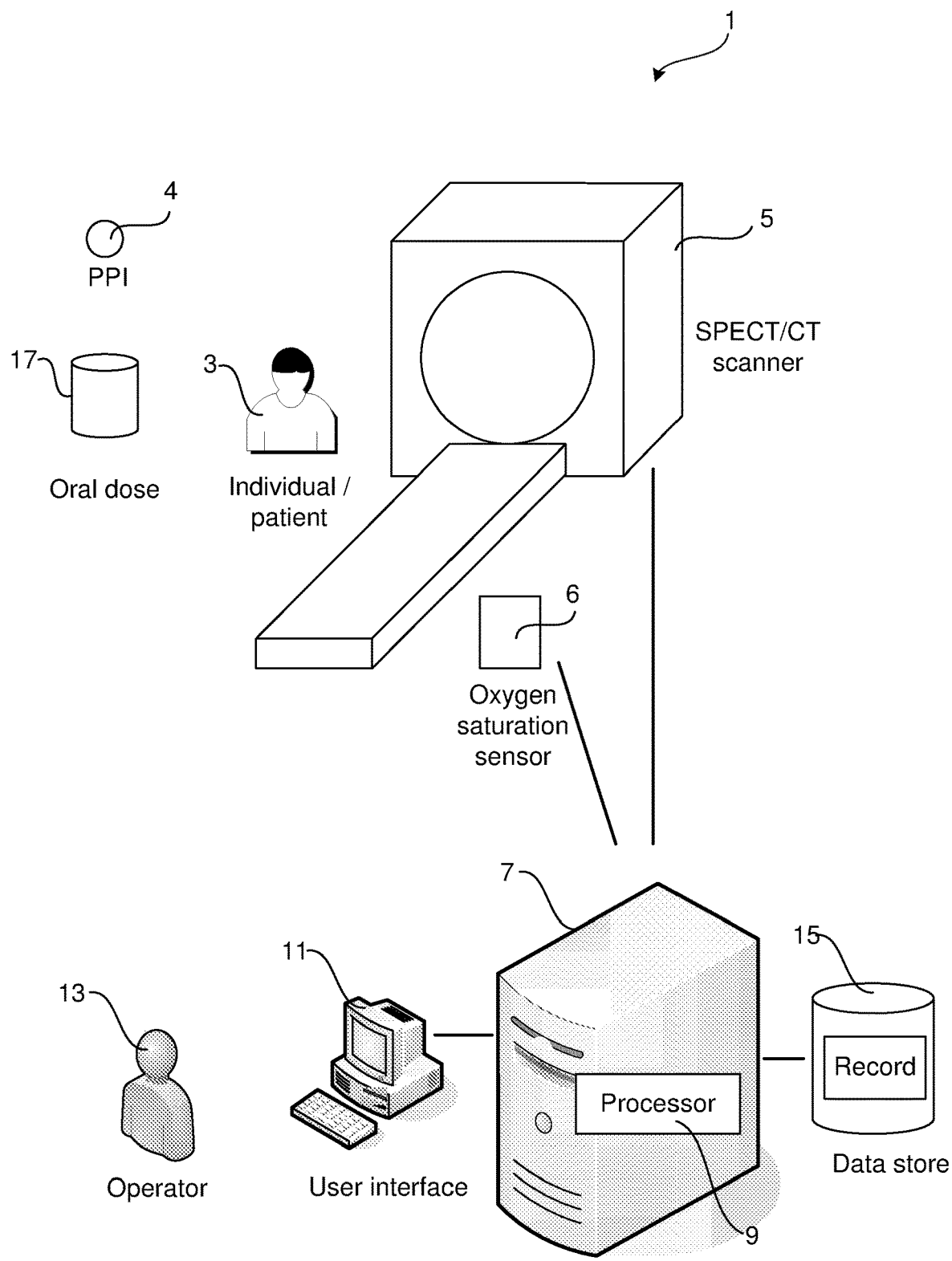
FIG. 1 is a schematic of a system for diagnosing reflux disease in an individual.

An example of the present disclosure will now be described. FIG. 1 illustrates an example of a system 1 for diagnosing reflux disease in an individual 3 with scintigraphy. The system 1 includes a single photon emission computer tomography (SPECT) scanner 5 and a computing device 7 including a processing device 9 and a user interface 11 for an operator 13. In some examples, the SPECT scanner 5 is a SPECT/CT scanner 5 that further includes x-ray computer tomography (SPECT/CT). The system 1 may also include a data store 15 associated with the computer 7.

The present disclosure includes a method 100 of administering 110 an oral dose 17 of tracer to the individual 3. The oral dose may include 75 mL to 200 mL of water. In some examples, the tracer includes technetium diethylenetriaminepentacetate (99mTcDTPA) tracer in the range of 40 to 100 MBq and, in some examples, 40-60 MBq of technetium phytate for the delayed study.

In another example a single oral dose of tracer is administered. This may include a single oral dose of technetium phytate in the range or 60 to 100 MBq. In some examples, the single oral dose of tracer may be preceded by administration of proton pump inhibitors (PPI) 4.

Figure 5:
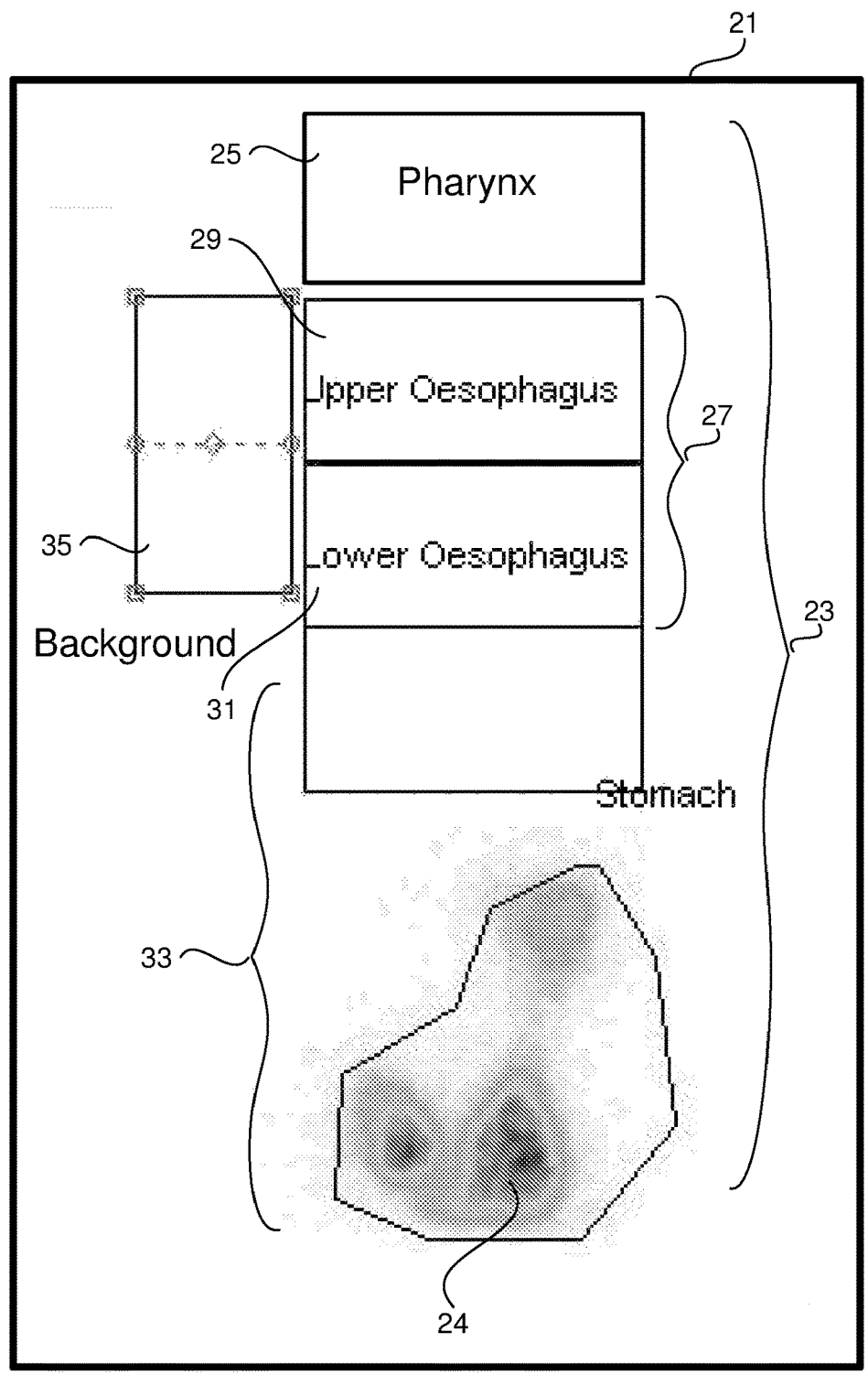
FIG. 5 is an example of an image frame from data captured by a SPECT scanner showing tracer activity in the stomach.

The SPECT/CT scanner 5 captures 120 data representative of multiple image frames 21 of the individual 3 in areas of interest 23 that includes the pharynx 25 and oesophagus 27. The data representative of the multiple image frames 21 are captured over time after administration of the oral dose 17. An example of an image frame 21 is illustrated in FIG. 5.

An oxygen saturation sensor 6 captures data on the oxygen saturation of the blood of the individual over time.

The processing device 9 may determine 130 one or more trend(s) in tracer activity over time in the areas of interest based on the data representative of multiple image frames 21. Each image frame 21 may have a sampling time of greater than 5 seconds and less than or equal to 60 seconds. The processing device 9 may also determine a trend in the oxygen saturation of the blood.

The individual 3 is classified as having reflux disease based on the trend(s) in tracer activity over time. For example, if it is determined that there is an ascending or flat trend in tracer activity over time in the oesophagus, this may be indicative of tracer in the oesophagus and that the individual has gastro oesophageal reflux disease (GORD). In another example, where it is determined that there is an ascending trend in tracer activity over time in the pharynx, this is indicative of aspiration of the tracer and that the individual has laryngopharyngeal reflux (LPR).

In some examples, the frequency of the trend in tracer activity in the pharynx that is above a specified threshold or in a specified range is determined. A higher frequency of the tracer activity above the specified threshold or in a relatively high specified range may be indicative of intermittent laryngopharyngeal reflux. A lower frequency of tracer activity above the specified threshold or a single extended occurrence may be indicative of continuous laryngopharyngeal reflux. In a further example, an indication of intermittent laryngopharyngeal reflux and a decreasing trend in oxygen saturation over time is indicative of a reflux mediated laryngopharyngeal spasm.

In some examples, the amplitude and/or time the trend in tracer activity is above a second specified threshold is indicative of a severity of laryngopharyngeal reflux.

The area of interest 23 may also include the stomach 33. Thus the processing device 9 may determine the trend in tracer activity in the stomach over time. This may include determining, a time to half clearance of gastric liquids in the stomach based on the tracer activity. This time may be used to classify whether the individual has prolonged liquid gastric emptying. In some examples this may include comparing the half time to clearance of gastric liquids with a threshold value.

Figure 11:
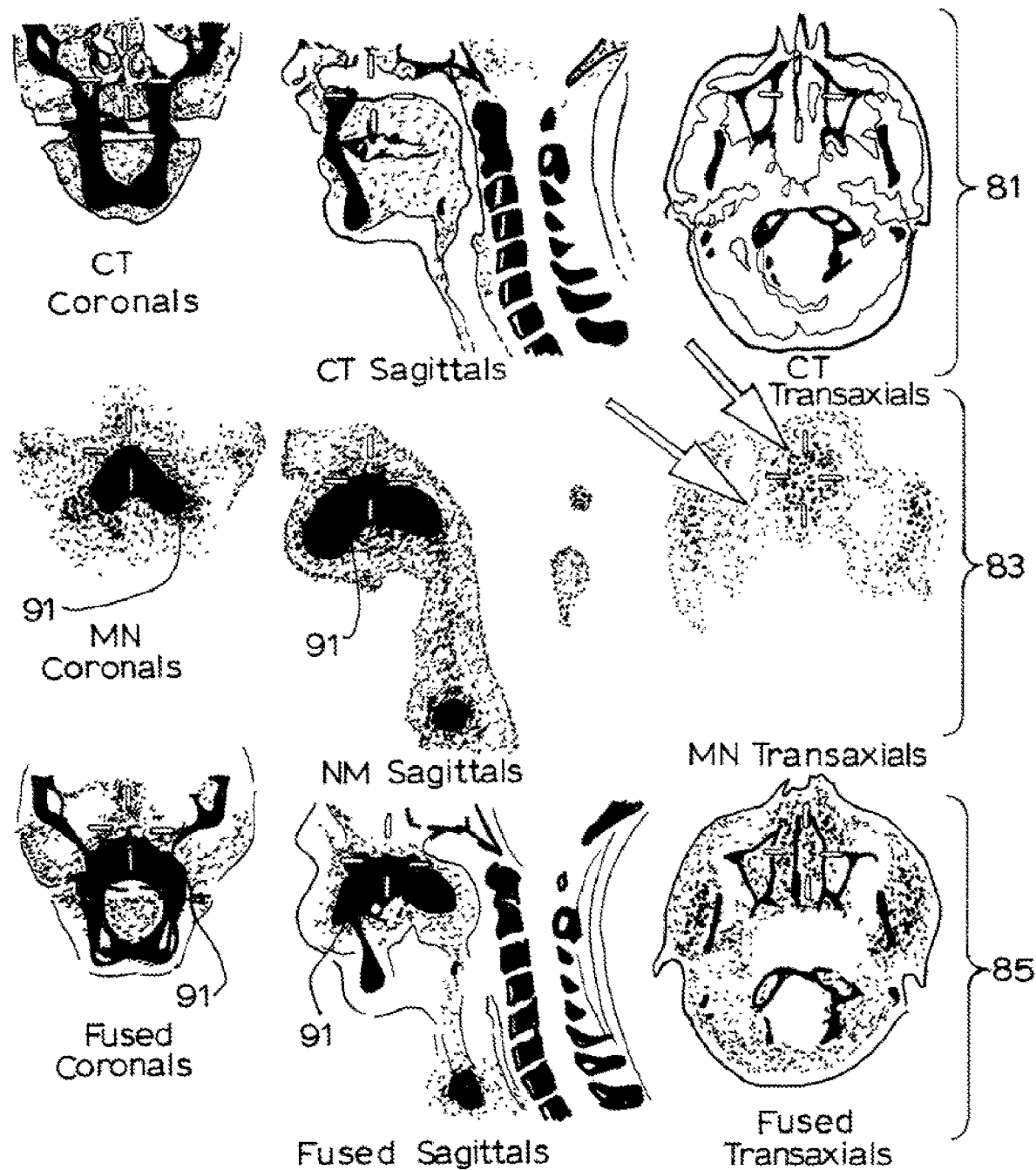
FIG. 11 shows example representations of CT images, SPECT images and combined SPECT/CT image showing tracer activity in respective areas of interest.
Figure 12:
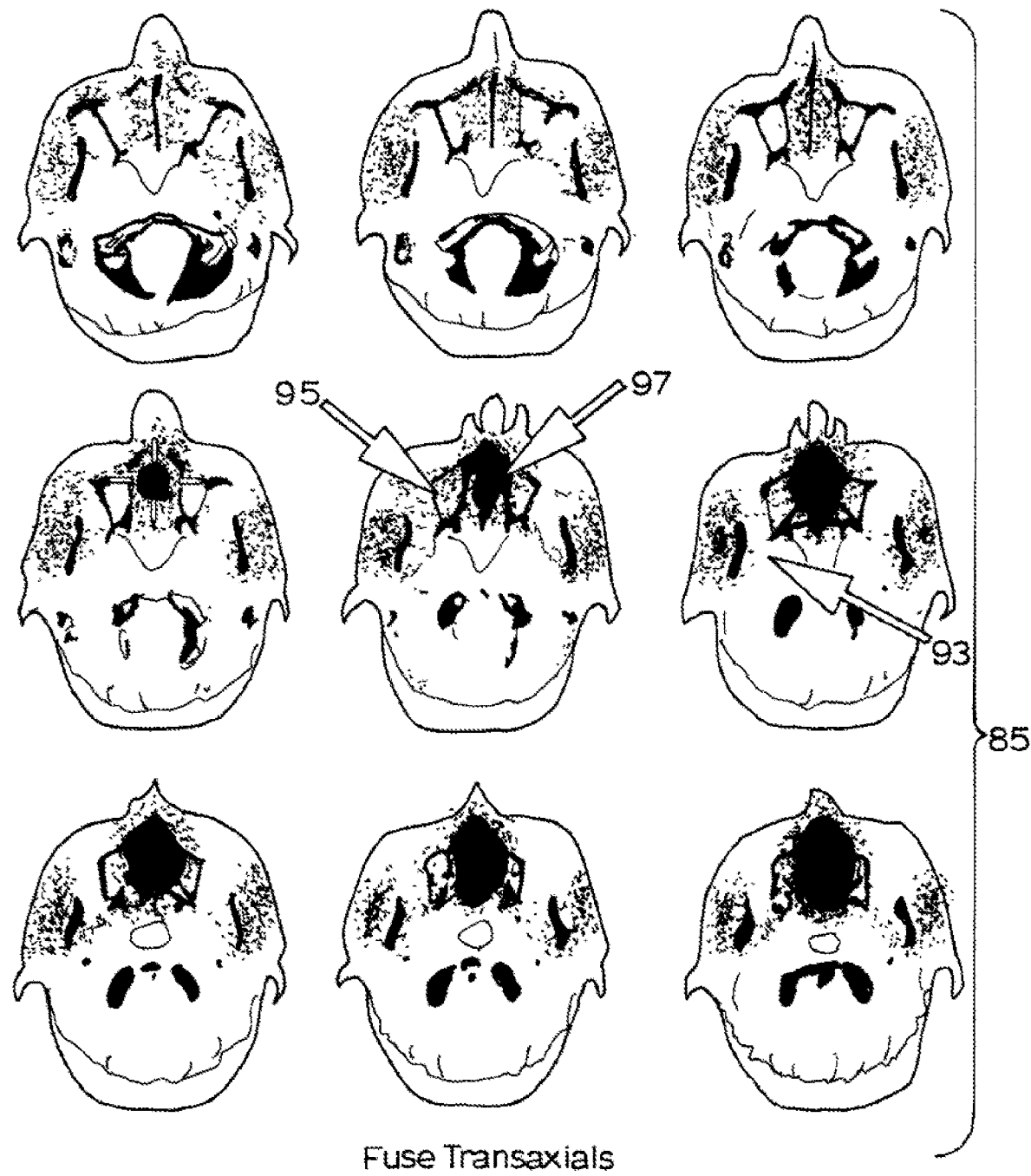
FIG. 12 shows other example representations of combined SPECT/CT images that show tracer activity from aspiration of tracer in areas of interest.

Based on the final delayed study (such as the study in a third time period discussed later) there is the option to include fused SPECT/CT images of the head and neck. The area of interest may also include one or more of the nasal turbinates, maxillary sinuses, Eustachian tube and/or middle ears. The system 1 may include generating one or more representations of the tracer activity overlayed to provide a combined SPECT/CT image such that tracer activity at the nasal turbinates, maxillary sinuses, Eustachian tube and/or middle ears can be visually identified at the corresponding anatomical areas of interest as illustrated in FIGS. 11 and 12. Tracer activity at these areas may be indicative of refluxate contaminating the sinuses, nasopharynx, eustachian tubes, middle ear and LPR. Furthermore, this may be indicative of potential areas of damage caused by refluxate and/or areas that require treatment.

The method 100 and system 1 of scintigraphy allows a diagnostic window to reflux disease that may include both GORD and LPR. In addition, it may allow the functional analysis of gastric emptying of liquids in the stomach which may contribute to the frequency and severity of GORD. The delayed third phase (e.g. third period study) allows assessment of refluxate aspirated into the lungs.

Furthermore the present method 100 and system 1 may produce SPECT/CT images of other areas that allow identification of refluxate contaminating the nasopharynx, nasal turbinates, maxillary sinuses, eustachian tube and middle ear. In such instances, the method and system provide visual evidence of the frequency and degree of reflux entering the oesophagus with subsequent contamination of the nasopharynx and adjacent structures and with anatomical registration in the corresponding SPECT/CT images. This is in contrast with known methods where there are difficulties in identifying such contaminates, let alone providing a visual representation of the location of contaminates at the respective anatomical areas.

Oral Dose of Radioactive Tracer 17

The oral dose of radioactive tracer includes a radioactive isotope which, by nuclear decay, emits radiation. In particular, this includes emitting gamma radiation. When in use, the emitted radiation from the tracer is herein described as tracer activity.

The type of radioactive isotope for the tracer may be selected from one that has a short half-life. In some examples, this may include technetium-99m that has a half-life of 6 hours. In some examples, the technetium-99m isotope in the tracer may be in the form of diethylenetriaminepentacetate (99mTcDTPA) and technetium 99m phytate.

In some particular examples, the 99mTcDTPA in the oral dose of tracer has radioactivity in the range of 40 to 100 MBq and the 99m TC Phytate in the range of 40-100 MBq. In some further examples, the radioactivity is in the range of 40 to 60 MBq. In yet another example, the oral dose of tracer is technetium phytate with radioactivity in the range of 60 to 100 MBq.

The oral dose of radioactive tracer may be in 75 mL to 200 mL of water to be administered to the individual. In some examples, the oral dose may be in around 75 mL to 100 mL of water. In yet other examples, the oral dose may be in around 100 mL to 200 mL of water. In another example, the oral dose may be in around 100 mL to 150 mL of water. In another example, the oral dose may be around 150 mL to 200 mL of water.

In some alternatives, other radioactive isotopes or a mixture of radioactive isotopes may be used. This may include iodine-123, iodine-131, 67 Gallium and/or indium-111. These radioactive isotopes may be in one or more compounds.

In some examples described herein, multiple oral doses of tracer 17 are administered. However, in some alternatives, a single dose of technetium phytates with radioactivity in the range of 60 to 100 MBq is administered. A single dose may reduce the radiation dose to the body, as technetium phytates is not absorbed and remains in the gastrointestinal tract and is excreted faecally. In some examples, using technetium phytate as the tracer may be desirable as it may be more stable in the stomach environment, unlike DTPA which increasingly breaks down unless it is freshly reconstituted. The breakdown of DTPA may contaminate results with entry of tracer (technetium pertechnetate) into the blood compartment with uptake in the thyroid gland and the salivary glands and stomach.

Proton Pump Inhibitors (PPI) 4

In some examples, the individual is administered proton pump inhibitors (PPI) before the oral dose of tracer. This may include taking PPI that is part of PPI therapy of the individual. This may include the individual taking the PPI in the morning before testing. This may typically be between 30 to 90 minutes before swallowing the radioactive tracer 17. If PPI are not taken, or ceased to be taken, this may lead to a rebound in stomach acid which subsequently degrades the technetium phytates and increases the level of background activity—which may degrades the results. It is to be appreciated in some examples, administration of PPI is optional and desirably administered to maintain individuals who are already on PPI therapy.

Examples of PPI may include omeprazole, lansoprazole, and pantoprazole.

The principal method by which the PPI therapy works is by reducing the volume of acid produced by the stomach and increasing the pH of the stomach towards a neutral level of approximately 7 pH. However, if the PPI therapy is ceased overnight, there is a rebound in acid formation in terms of both the volume and the reduction in pH towards 4.0. In this acidic environment, DTPA invariably breaks down and there is some degradation of the technetium label from the phytates. The main problem that results from the breakdown of the imaging agent is that uptake in the salivary glands and thyroid gland can be mistaken for refluxate by an inexperienced reader. The second issue is that the free pertechnetate is taken up by the stomach and can interfere with the accuracy of the liquid gastric emptying study. i.e. Falsely make it longer than it really is, although this is a relatively minor issue. The quality control in the image is simple in that the planar or two-dimensional study will clearly show uptake of tracer in the parotid salivary glands and in the thyroid gland, allowing the reader to be more careful when they are interpreting the SPECT/CT images.

Gamma Camera/SPECT/CT Scanner 5

A gamma camera or other system that can detect gamma radiation at specific locations may be used to detect tracer activity (i.e. the gamma rays emitted by the ingested tracer). In some examples, this may include using a single photon emission computer tomography (SPECT) scanner.

An example of a SPECT scanner includes the General Electric Millenium™ system (General Electric®, Milwaukee, USA).

In some further examples, the SPECT scanner may also include x-ray computer tomography (CT) as a SPECT/CT scanner 5. This may allow construction of images that combine detected tracer activity (from the SPECT image) along with anatomical features (from the x-ray CT image).

An example of a SPECT/CT scanner includes the General Electric Hawkeye 4™ system (General Electric®, Milwaukee, USA).

As will be discussed in further detail, the scanner 5 is used to capture data representative of multiple image frames of the areas of interest over time. In some examples, each image frame is representative of detected tracer activity during a sampling time. Successive image frames over time may then make up the multiple image frames.

The sampling time may be in the range of greater than or equal to five seconds and less than or equal to sixty seconds. In some examples, the sampling time is greater than or equal to fifteen seconds and less than or equal to thirty seconds. In some examples, the sampling time is around fifteen seconds and in such examples, four sequential image frames may be captured every minute.

In some examples, the SPECT/CT scanner 5 may operate with a shorter sampling time (i.e. higher frequency). For example, the SPECT/CT scanner 5 may have a sampling time of one second. However, it is to be appreciated that data obtained from a scanner 5 having a sampling time of one second may be used to determine an image frame with a higher sampling time. For example, data in relation to fifteen consecutive one second captures may be aggregated to provide an image frame with a sampling time of 15 seconds.

Oxygen Saturation Sensor 6

An oxygen saturation sensor 6 is used to assess oxygen saturation of the blood of the individual. This may include a finger-based sensor (such as a pulse oximeter) to measure oxygen saturation for the time periods during the methods. In some specific examples, this includes measuring and determining the trends in oxygen saturation during the time periods where the individual is in the supine position. The oxygen saturation sensor 6 may be in communication with the computing device so that rapid changes in the oxygen saturation level during the period of acquisition of the trends in tracer activity (and respective image frames). This can be used to determine correlation of the oxygen saturation to the degree and frequency of reflux that is occurring in the laryngopharyngeal region at the respective times.

Computing Device 7 and Processing Device 9

The SPECT/CT scanner 5 and, in some examples the oxygen saturation sensor 6, may be in communication with a computing device 7. The computing device 7 may be in the form of desktop computer, laptop computer, and/or a mobile communication device such as a tablet computer, smartphone, etc. The computing device 7 has a processing device 9 and is associated with a user interface 11 that may include a display, printer, and inputs such as a keyboard, keypad, buttons, mouse, touchscreen, etc.

Detailed Description of the Method

Figure 2:
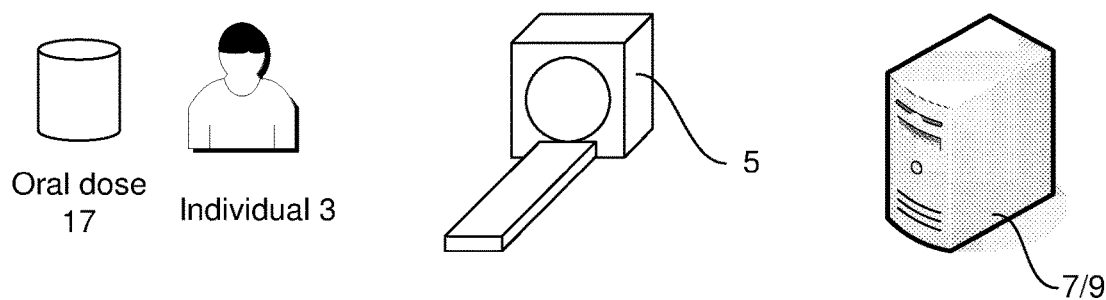
FIG. 2 is a flow diagram of a method for diagnosing reflux disease in an individual.
Figure 3:
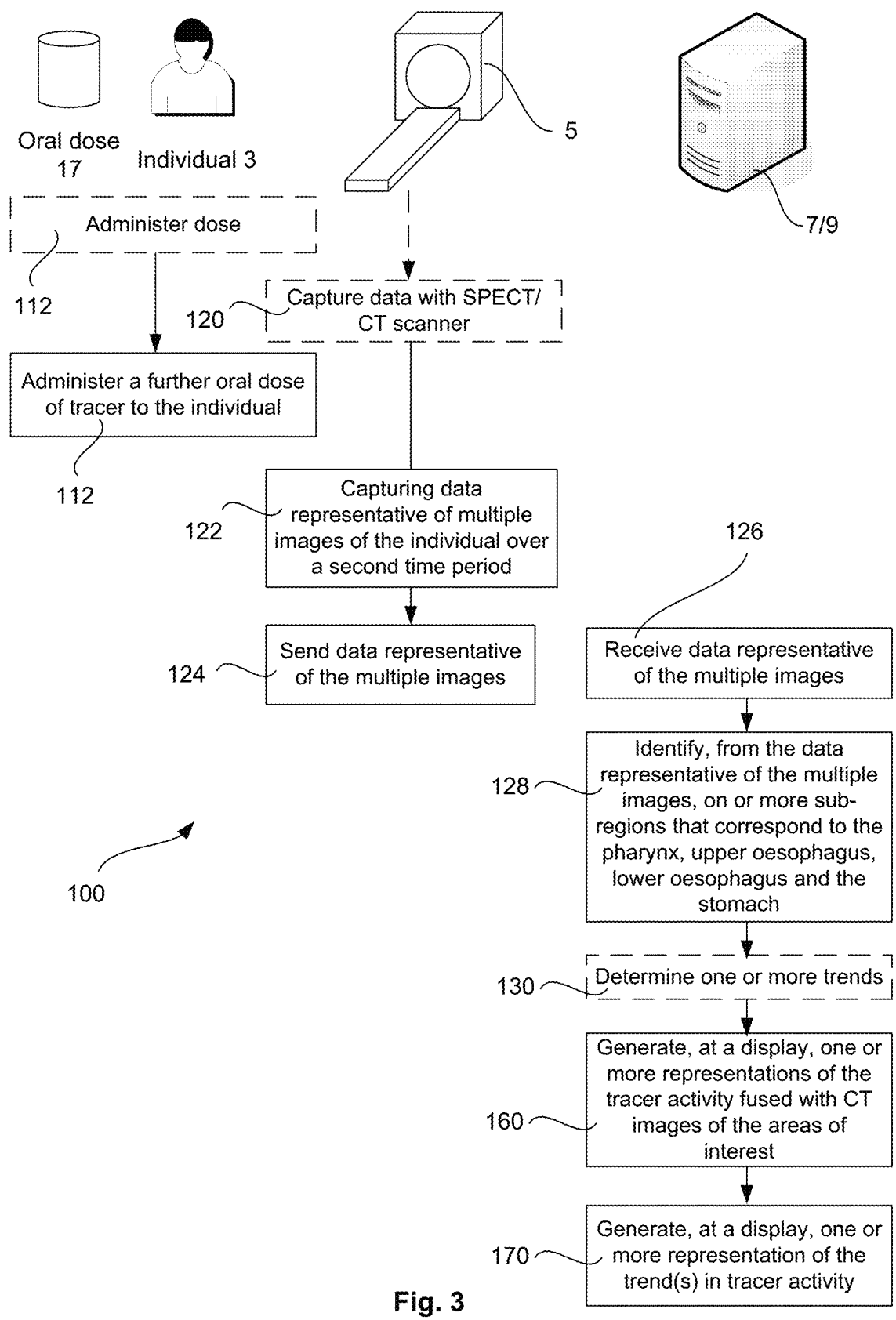
FIG. 3 is a flow diagram of further steps in one example of the method in FIG. 2.
Figure 4:
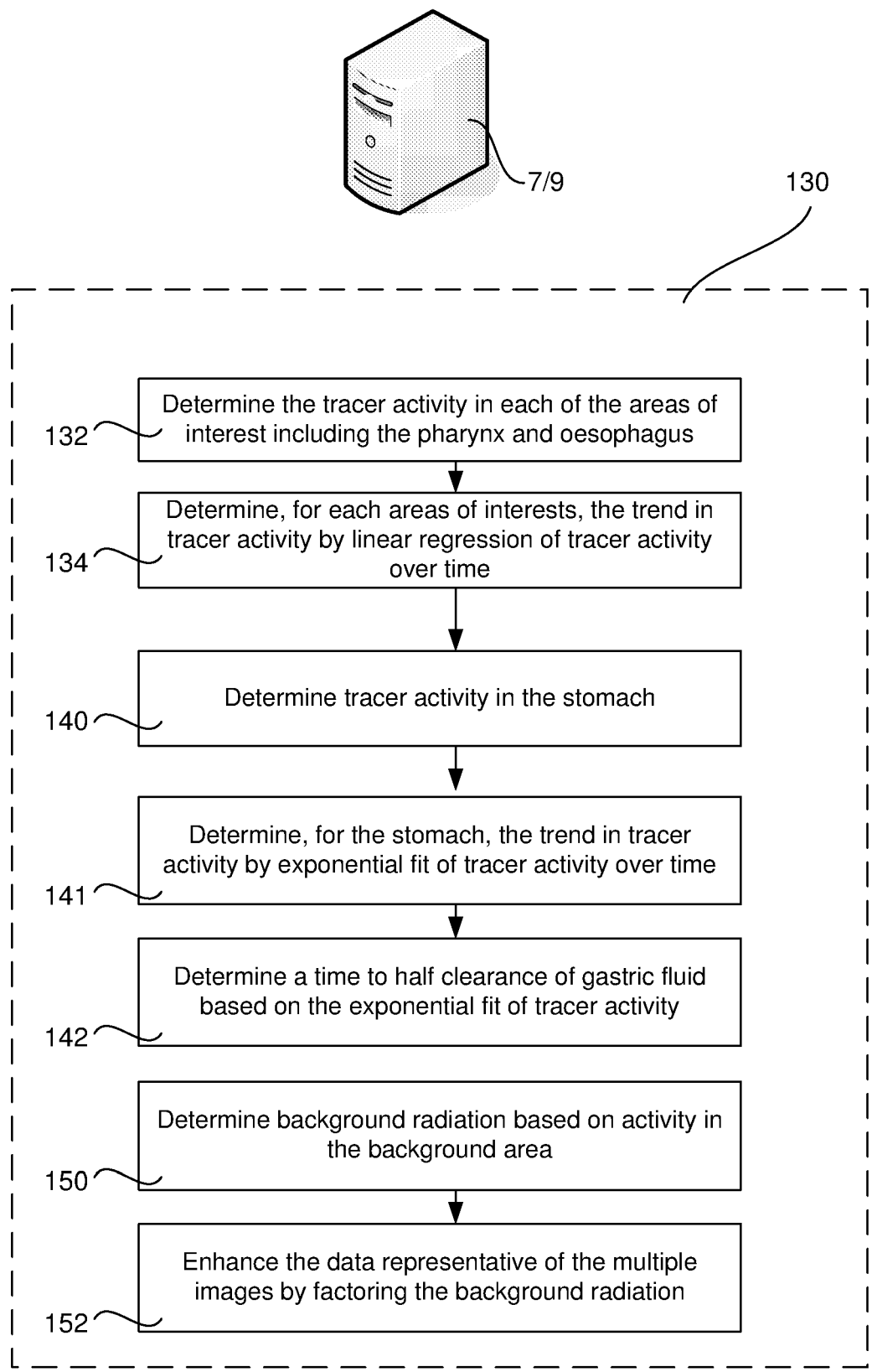
FIG. 4 is a flow diagram of example steps to determine one or more trend(s) in tracer activity of the method in FIG. 2.

The method 100 of diagnosing reflux disease in an individual will now be described with reference to FIGS. 2 to 4.

Administering an Oral Dose of Tracer 110

An oral dose of tracer 17, as described above, is administered to the individual 3. This is swallowed orally and, in some examples, with the individual 3 in the upright position.

The oral dose of tracer 17 may be followed by a flushing of water to clear the mouth and oesophagus of the radioactive tracer. In some examples the flushing of water may be in the range of 50 mL to 75 mL of water.

Example 1—Single Oral Dose

In some examples, a single dose of tracer 17 is swallowed, such as an oral dose of technetium phytates in the range of 60 to 100 MBq of water. This may be followed by a flushing of water as described above.

Figure 15:
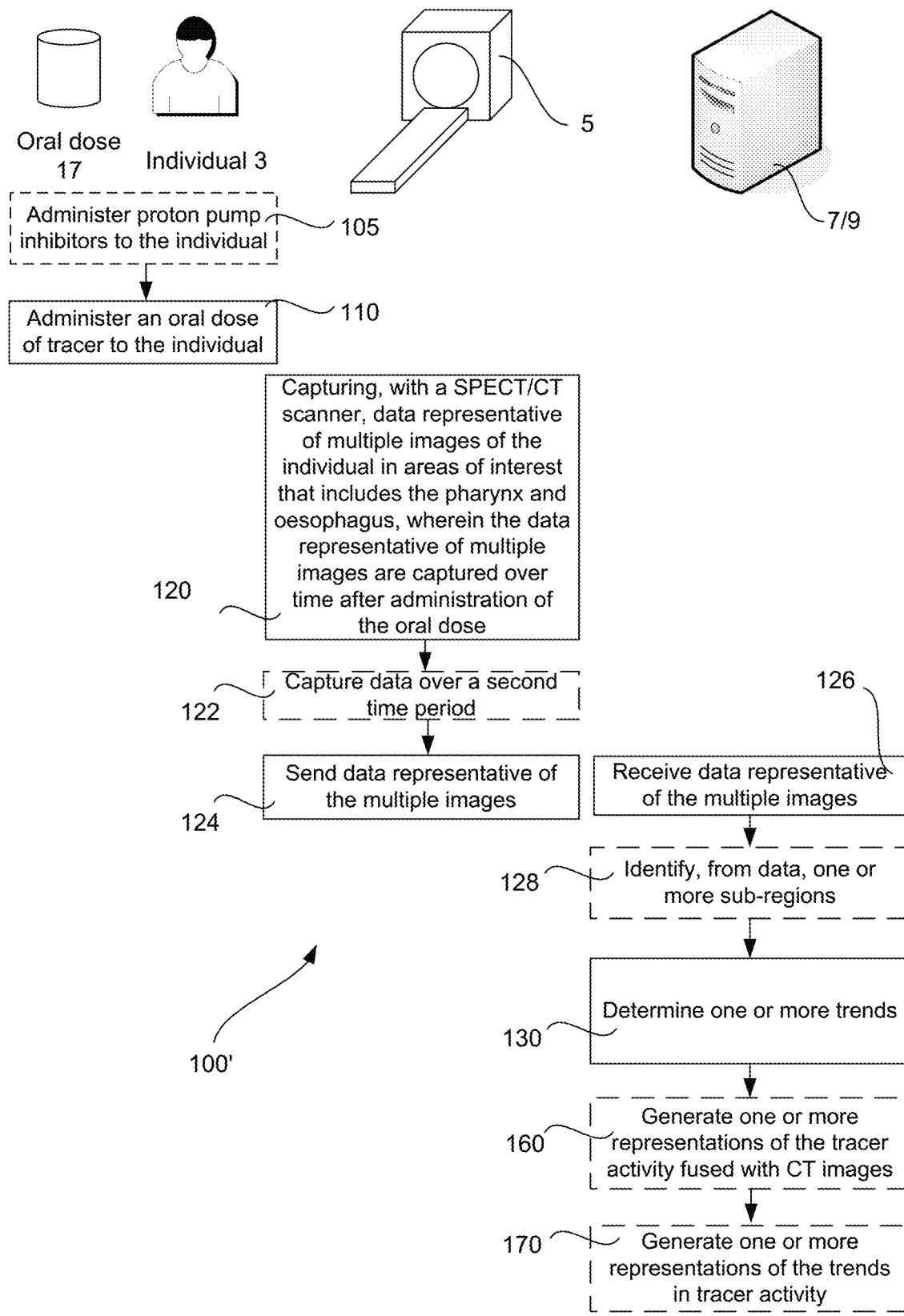
FIG. 15 is a flow diagram of another example of the method for diagnosing reflux disease in an individual.

In one variation, PPI is administered 105 before the single dose of tracer 17 to reduce the pH of the stomach (and to reduce potential bread down of the dose of tracer 17). This may include taking PPI in accordance with PPI therapy of the individual. This is illustrated in the variation of the method 100' as shown in FIG. 15.

It is to be appreciated that administration of PPI may, in some circumstances, be optional depending on the diagnosis of existing medical conditions of the individual 3.

Example 2—Multiple Oral Doses

In another example, multiple doses of tracer 17 are administered to the individual. For example, after acquisition of the erect and supine dynamic studies (such as those of the first and second period), a further dose of technetium 99m Phytate (40-100 MBq) is administered in 75 to 100 mL of water with a flush of 50-75 mL of water to clear radioactivity from the mouth and oesophagus. This is to assess for contamination of the extra-oesophageal structures by refluxate 2 hours later with imaging by anterior and posterior scintigraphic images of the chest and acquisition of the tomographic SPECT/CT images of the head and neck. e.g. LPR or lung aspiration. This compound is not absorbed into the circulation and excreted as occurs with DTPA so remains in situ to indicate contamination by refluxate.

Capturing Data Representative of Multiple Image Frames 120, 122

A gamma camera, or similar device such as the SPECT scanner 5, captures data representative of multiple image frames 21 of the individual in areas of interest. The multiple image frames represent data captured over time after administration of the oral dose.

Figure 6:
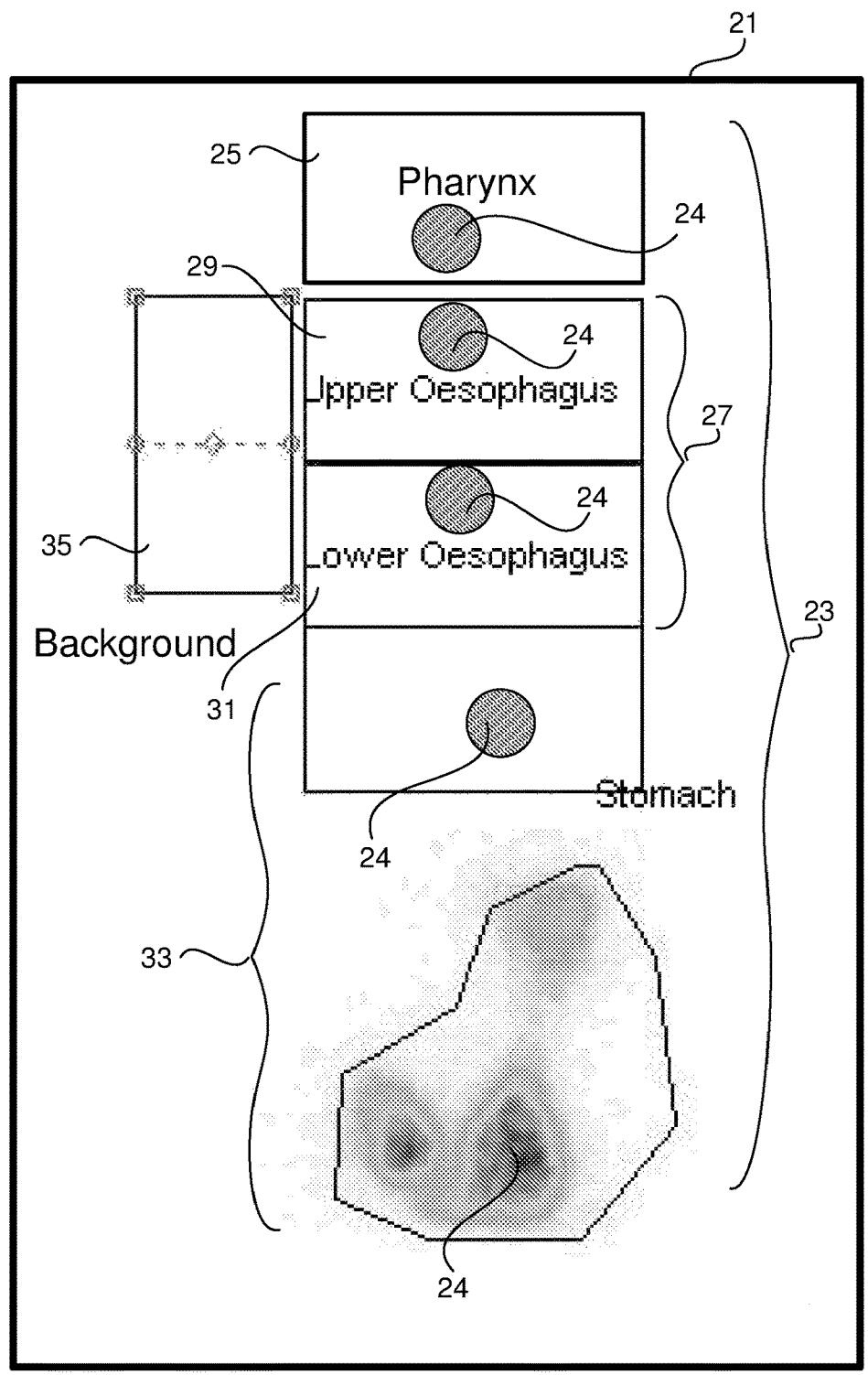
FIG. 6 is an example of another image frame from data captured by a SPECT scanner showing tracer activity in other areas of interest.

An example of an image frame 21 is illustrated in FIG. 5 that shows tracer activity 24 in respective areas of interest 23 of the individual 3. Another example of an image frame 21 is illustrated in FIG. 6.

Capture of Data Over a First Time Period

In one example, data is captured over a first time period that is up to between five minutes and thirty minutes after administration of the oral dose. In some examples, the first time period commences as soon as practicable after administering the oral dose 110 and this may include commencing the first time period within one minute after administering the oral dose. In some examples, the first time period may commence within thirty seconds of administering the oral dose. In yet further examples the first time period may commence within 15 seconds or less of administration of the oral dose.

During data capture 120 over the first time period the individual may be in the upright position (and an example of the data will be discussed below with reference to FIG. 7). The data representative of the multiple image frames captured during the first time period may be used to determine conditions indicative of GORD which will be discussed in further detail below.

Capture of Data Over a Second Time Period

In a further example, data may also be captured 122 over a second time period. The second time period may occur up to 30 minutes after administration of the oral dose. In some examples, the second time period commences after capture in the first time period and for a period of around thirty minutes.

During data capture 122 over the second time period the individual may be in the supine position (and an example of the data will be discussed below with reference to FIG. 8). The data representative of the multiple image frames captured during the second time period may be used to determine conditions indicative of aspiration of the tracer and LPR which will be discussed in further detail below.

Capture of Data Over a Third Time Period

In a further example, data may also be captured 122 over a third time period. The third time period may occur between ninety and one hundred and fifty minutes after administration of the oral dose. In some examples the third time period occurs over a thirty minute period. In some examples, the third time period commences approximately one hundred and twenty minutes after administration of the oral dose.

During data capture 122 over the third time period the individual may be in the supine position (and an example of the data will be discussed below with reference to FIG. 9). The data representative of the multiple image frames captured during the third time period may be used to determine conditions indicative of aspiration of the tracer and LPR which will be discussed in further detail below.

In some examples, the method 100 may include administering 112 a further oral dose of tracer after the second time period (and in some examples, immediately after the second period). In some examples this may include an oral dose that includes an oral dose of 99mTc Phytate in the range of 40 to 100 MBq (and in some examples around 60 MBq) in approximately 50-75 mL of water. In some examples this further oral dose may be subsequently flushed with 50 mL of water. This further oral dose of tracer may assist in determining aspiration during the time between the second and third period (and during the third period).

Capture of Oxygen Saturation Data

Figure 16:
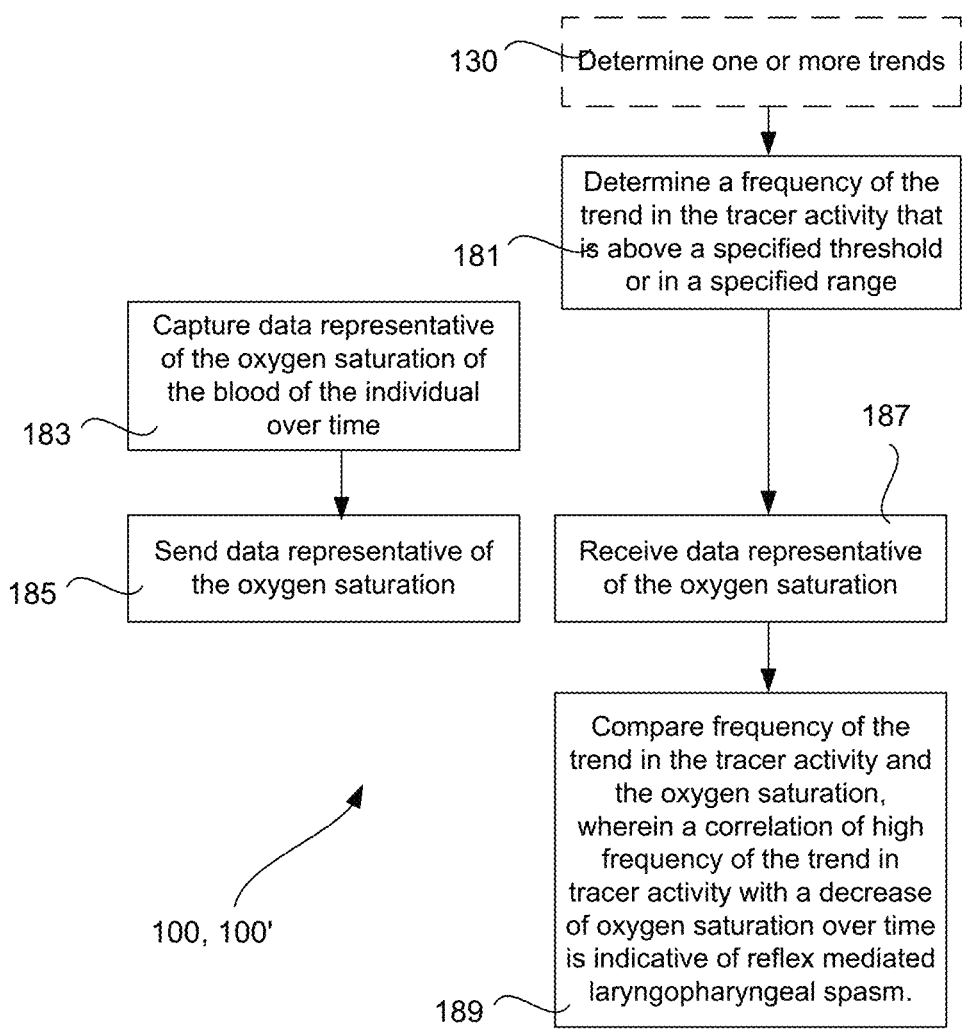
FIG. 16 is a flow diagram of further steps in the method for diagnosing reflux disease in an individual including determining a frequency of tracer activity, determining oxygen saturation and determining occurrence of reflex mediated laryngopharyngeal spasm.

Referring to FIG. 16, the method 100,100' may also include capturing 183, with the oxygen saturation sensor 6, data representative of the oxygen saturation of the blood of the individual over time. This may include any one or more of the time periods described above. Oxygen saturation data is sent 18 from the oxygen saturation sensor 6 (or other pulse oximetry device) where it is received 187 at the computing device 7.

Determining One or More Trends 130

FIGS. 5 and 6 illustrate representations of captured image frames 21 of an individual in areas of interest 23. For example, FIG. 5 shows a single image frame 21 with tracer activity 24 in the areas of interest 23 during over one sampling time period.

In some examples, processing device 9 divides the areas of interest 23 into respective sub regions. This may include the pharynx 25, upper oesophagus 29, lower oesophagus 31, and stomach 33. In some example, this may include the processing device determining respective areas in the image frame 21 that these anatomical areas are expected. In some example, this may be based on the operator 13 selectively defining boundaries in the image frame 21 for one or more of these anatomical features. In other examples, the processing device 9 may automatically determine these boundaries based on data received from the SPECT/CT scanner. For example, the x-ray CT may capture data related to these particular anatomical features and the processing device 9 may match the shape and/or size of the captured data to predict the location of pharynx 25, upper oesophagus 29, lower oesophagus 31 and stomach 33. In yet other examples, the operator 13 may provide characteristics of the individual (such as height, weight, or location of features such as chin, shoulders, collar bone, etc.) and the processing device 9 may determine the boundaries based on these characteristics.

In some examples the image frame 21 may also include data representative of a background area 35. The background area is an area located outside a fluid path of the nasopharynx, larynx and oesophagus 27. The processing device 9 may then determine the background radiation based on the activity in the background area. This may be used to enhance the multiple image frames 21 by factoring in background radiation (if any).

The data from the multiple image frames 21 can be used to determine one or more trend(s) that are indicative of reflux disease. FIG. 5 is an example of an image frame 21 where most of the tracer activity is in the stomach 33. FIG. 6 is an example of another image frame 21, at a different time to FIG. 5, where some of the tracer (and hence tracer activity 24) has moved to other areas such as the oesophagus 27 and pharynx 25. Examples of determining these trends based on multiple image frames at different times will now be discussed below.

Determining Trends During the First Time Period

Figure 7:
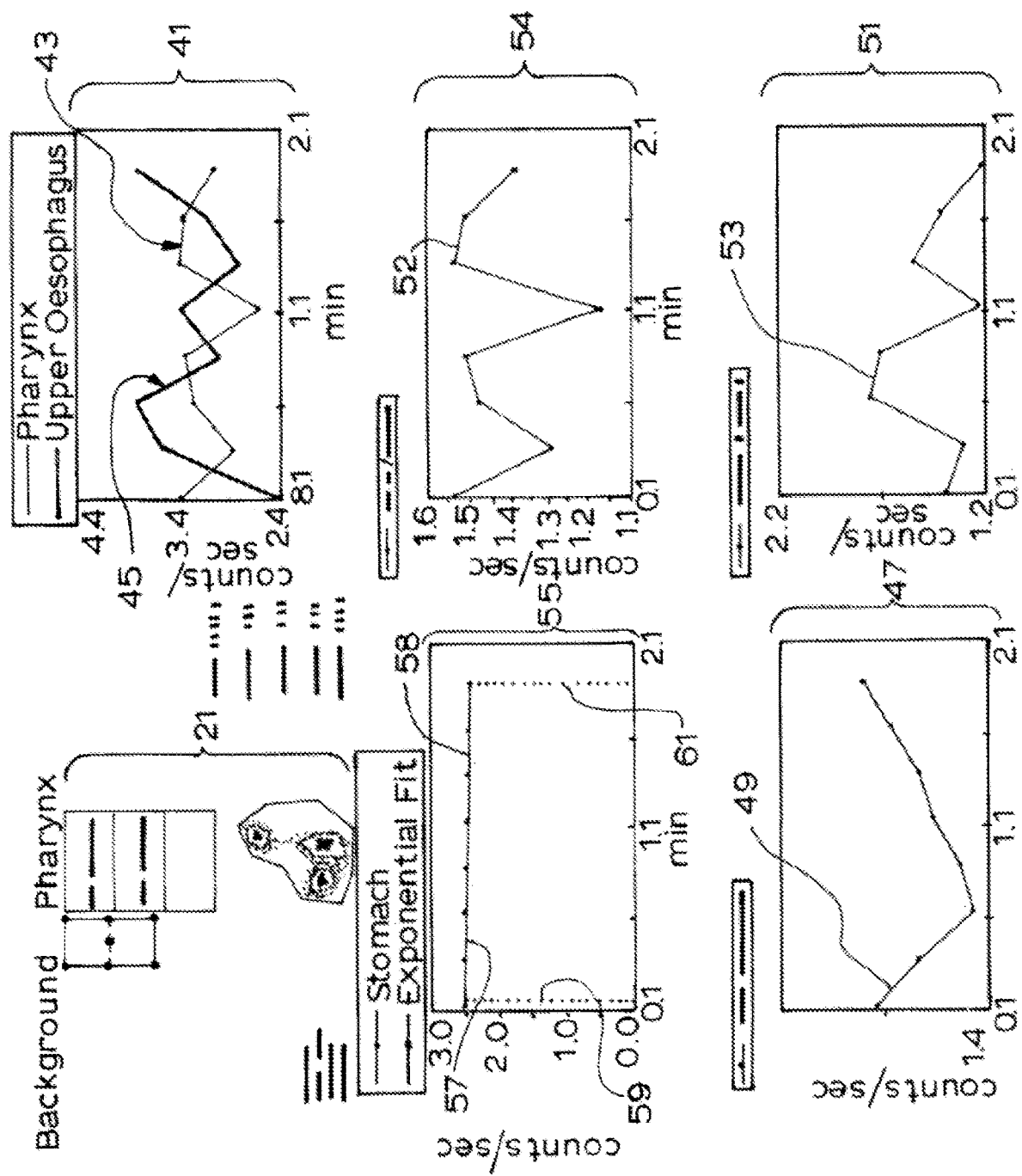
FIG. 7 is a graphical representation data captured during a first period with an individual in the upright position.

FIG. 7 illustrates an example representation of data during the first period (with the individual in the upright position) that may be generated at a display (at the user interface 11) for the operator 13 to review. This includes an exemplary image frame 21 that is indicative of the areas of interest and corresponding tracer activity. This also includes, graphically, representations of tracer activity in the areas of interest 27 at respective times, which in this example is in counts per second.

The detected activity 43 in the pharynx area 25 and the detected activity 45 in the upper oesophagus area 29 are illustrated in graph 41. Graph 41 shows these results as data points every fifteen seconds (that reflects the fifteen second sampling time) connected by linear interpolants. In some examples, the data points may reflect the number of activity counts detected over the fifteen second sampling time in the respective area divided by fifteen second to provide the counts per second result.

The detected and determined 150 activity 49 in the background area 35 is illustrated in graph 47. The capture of activity and graphical representation in graph 47 may use similar methods as described above for the pharynx and upper oesophagus graph 41. The background activity may be used to enhance 152 the captured data in relation to tracer activity by factoring in the background activity. For example, graph 51 illustrates enhanced detected activity 53 in the pharynx 25 where the background activity for during corresponding sampling time period is taken into account. This may include subtracting the detected background activity 49 from the detected activity 45. In other examples, taking the background activity into account may include dividing the detected activity 45 with the background activity 49 for the respective periods. In another example, the average (i.e. mean) background activity is used to enhance the detected activity 52 in the pharynx 25 as shown in graph 54. The detected activity 43, 45 (and respective enhanced versions) may be used to determine trends such as increasing, decreasing, or stable activity.

The detected activity 57 in the stomach area 33 is illustrated in graph 55. In this example, the activity is determined 140 with a sampling time of fifteen seconds to provide data points every fifteen seconds. A curve 58, based on determining 141 exponential fit of the data points, is provided which may be used to graphically illustrate the trend. Gastric emptying may be modelled as an exponential function and therefore the exponential fit of data points of the detected activity 57 may be appropriate. It is to be appreciated that in other examples, least squares fit, linear interpolation, etc. may be used instead of the curve 58. The graph 55 also shows a maximum 59 and a minimum 61 for the tracer activity in the stomach area 33 and this data may assist in determining gastric emptying as will be discussed in further detail below.

Determining Trends During the Second Time Period

Figure 8:
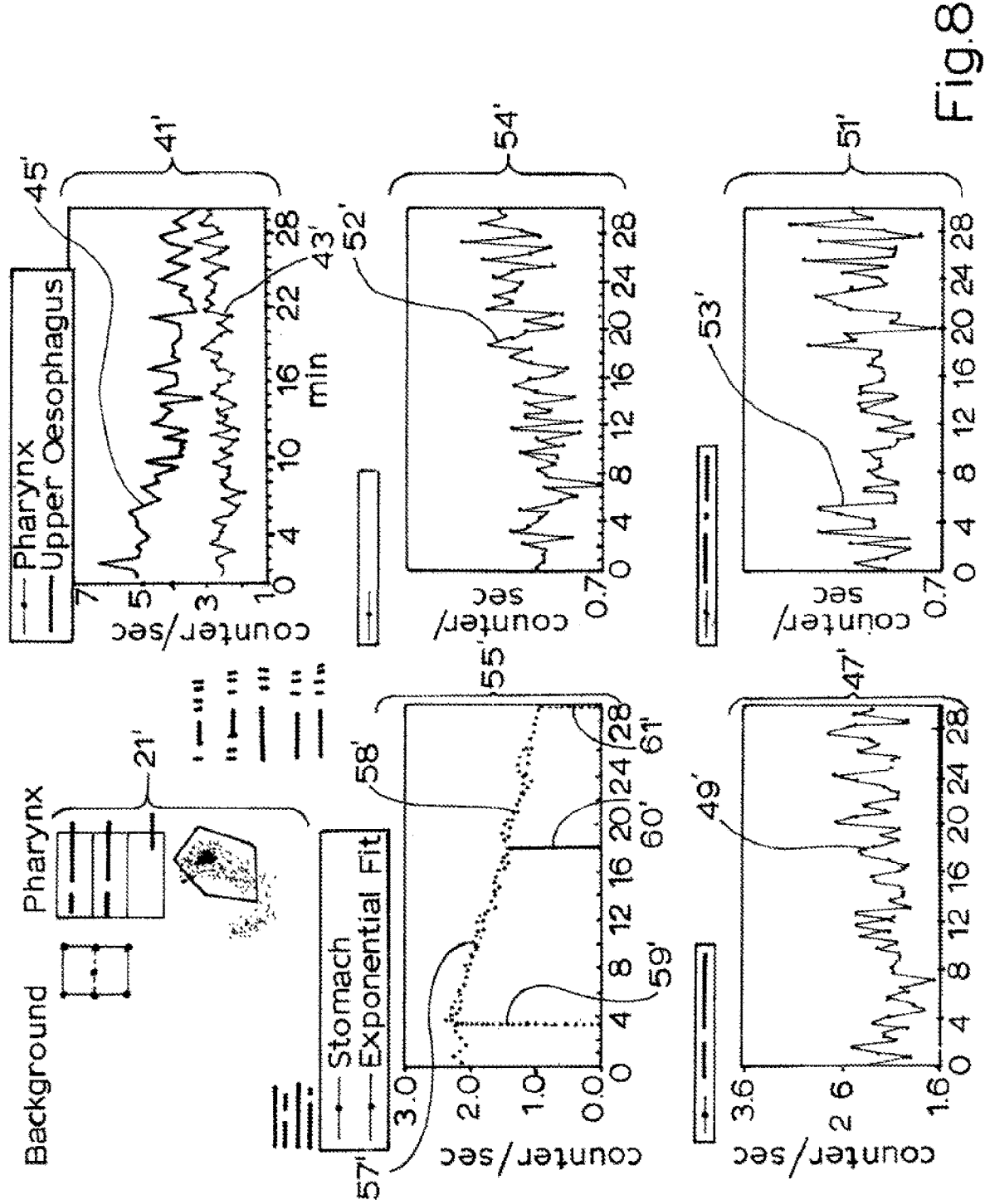
FIG. 8 is a graphical representation of data captured during a second period with the individual in the supine position.

FIG. 8 illustrates an example representation of data during the second period (with the individual in the supine position) that may be generated at a display (at the user interface 11) for the operator 13 to review. The features in FIG. 8 are similar to those in FIG. 7 but denoted with a prime. Referring to graph 41', there is an increasing trend in detected activity 43' in the pharynx area 25 over time (which in this example is over a thirty minute period). This is further enhanced by taking into account the background activity 49' as shown in graphs 51' and 54'. Referring back to graph 41', there is a decreasing trend in detected activity 45' in the upper oesophagus 29 over time. The detected activity 57' in the stomach area 33, and the fitted curve 58', show an exponentially decreasing trend over time. This curve 58', in conjunction with the maximum 59', may be used to determine the time to half clearance 60 of gastric liquid in the stomach 33.

Determining Trends During the Third Time Period

Figure 9:
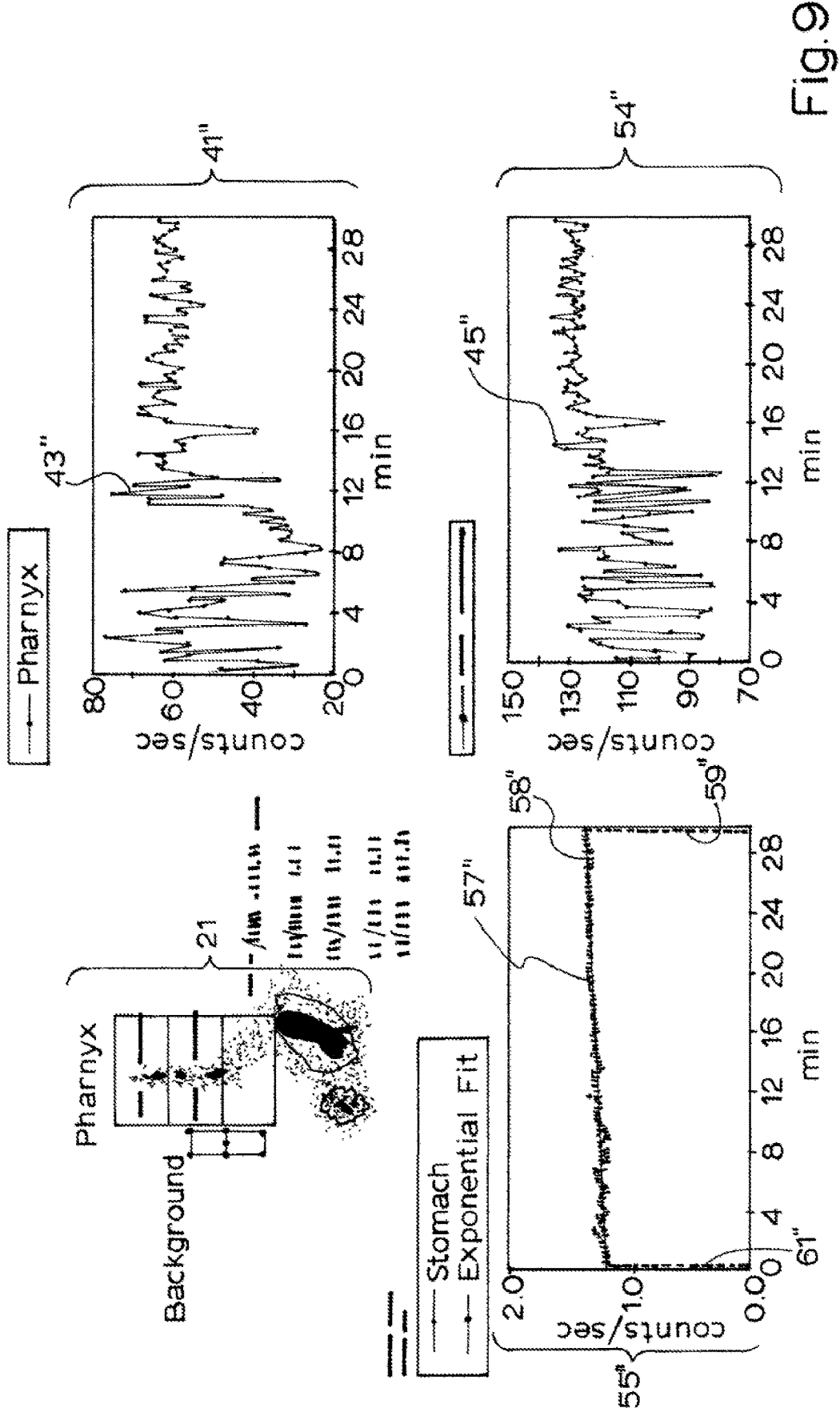
FIG. 9 is a graphical representation of data captured during a third period with the individual in the supine position.

FIG. 9 illustrates an example representation of data during the third period (with the individual in the supine position) that may be generated at a display (at the user interface 11) for the operator 13 to review. The features in FIG. 9 are similar to those in FIGS. 7 and 8 but denoted with a double prime. The time scale in these graphs commences at the beginning of the third time period. Therefore the 30 minute period in the illustrated time scale may start, for example, one hundred and twenty minutes after administration of the oral dose.

As shown in the graph 41", the tracer activity 43" in the pharynx area 25 is substantially higher during this third time period at around sixty counts per second. This is compared to the earlier time periods (as shown in FIGS. 7 and 8) that were under four counts per second.

As shown in graph 54", the tracer activity 45" in the upper oesophagus 29 is substantially higher during this third time period at around one hundred and thirty counts per second. This is compared to the earlier time periods (as shown in FIGS. 7 and 8) that were six counts per second or less.

Therefore the trend during the third time period, for this patient, is of increasing tracer activity in the pharynx 25 and upper oesophagus 29. This may be indicative of conditions including reflux disease(s) as described in further detail below.

Other Trends—Frequency and Severity of Reflux

In some examples, a frequency of reflux at the level of the pharynx is determined (in one or more of the above periods). In some examples, this includes determining 181 a frequency of the trend in tracer activity in the pharynx that is above a specified threshold, or in a specified range. Referring to FIG. 17 and graph 200, the trend in tracer activity 203 in the pharynx is plotted over time. The tracer activity 203, in this example, has a slight increasing trend that indicates instances of reflux to the pharynx. In addition, the tracer activity 203 crosses a specified threshold 205, multiple times. The instances of the tracer activity 203 crossing over the specified threshold is indicative of the frequency of reflux at the level of the pharynx.

In some alternatives, the frequency is determined based on tracer activity 203 in a specified range. This may include a value range for the tracer activity. This may be useful for removing outliers or erroneous readings.

A trend of tracery activity 203 that shows relatively high frequency above the specified threshold is indicative of intermittent laryngopharyngeal reflux. That is, laryngopharyngeal reflux occurring multiple times separated by times without reflux during the time period(s). A relatively lower frequency (or a single protracted occurrence) above the specified threshold may be indicative of continuous laryngopharyngeal reflux.

The frequency when the individual is in the supine position may be of particular importance.

In some examples, the amplitude and/or time of the tracer activity in the pharynx that is above the specified threshold (or a second specified threshold) is determined. The amplitude and/or time may be indicative of a severity of laryngopharyngeal reflux.

Other Trends—Oxygen Saturation

The oxygen saturation data may be recorded so that trends in the oxygen saturation over time can be determined by the computing device 7. This may include neutral trends, decreasing trends over time, and/or oscillating oxygen saturation over time (i.e. multiple periods of relatively lower and higher oxygen saturation). Referring to graph 207 in FIG. 17, this illustrates an example where the oxygen saturation 209 is decreasing over time.

Summary of Results

Figure 10:
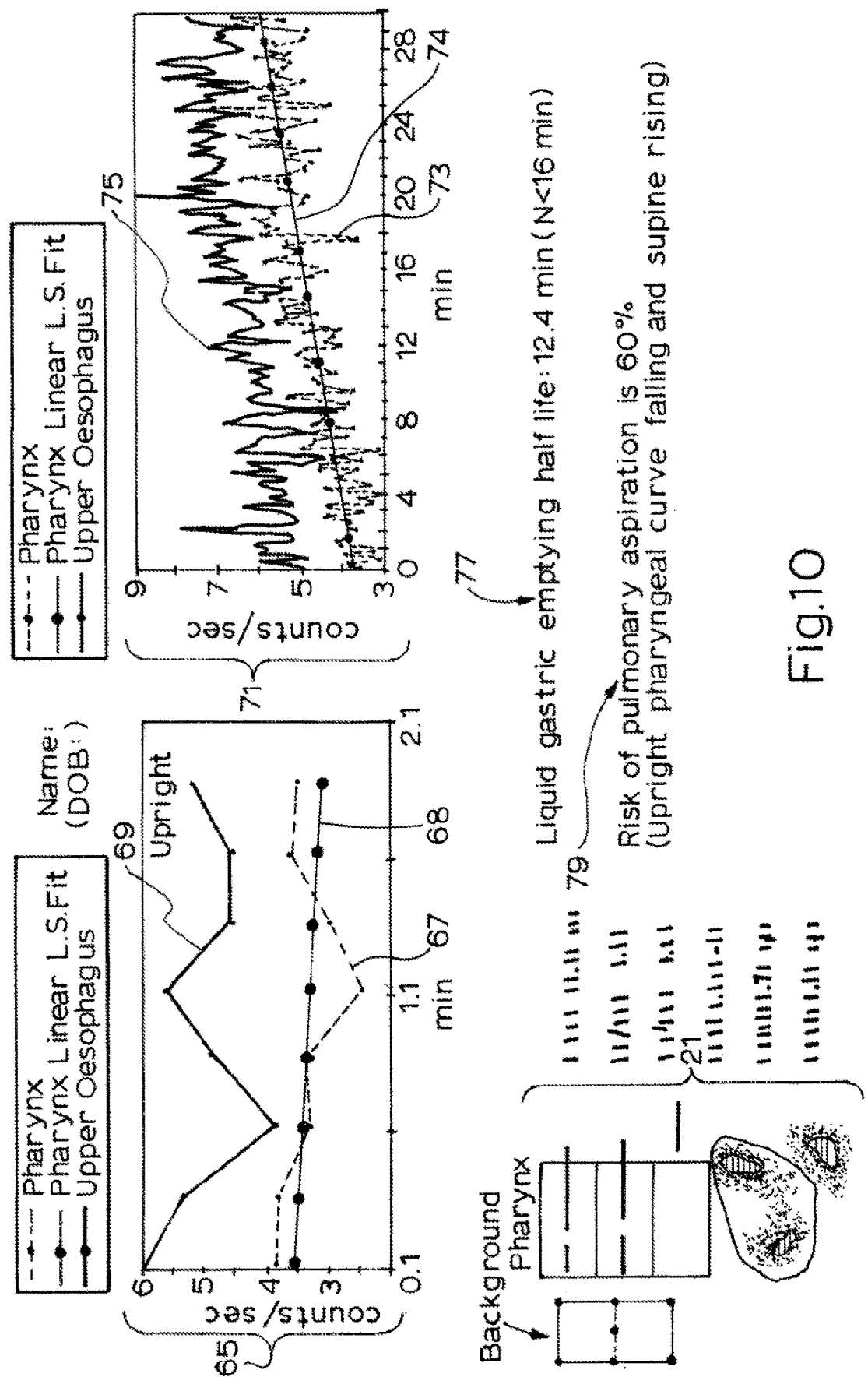
FIG. 10 is an example representation of a summary of the upright and supine data captured by the system.

FIG. 10 illustrates an example representation of a summary of the upright and supine data that may be generated at a display (at the user interface 11) for the operator 13 to review. This may include a summary of the results during the first period in the upright position as shown in graph 65. Graph 65 includes the tracer activity 67 in the pharynx area 25 and linear regression (in this case a linear least squares fit) line 68 of that tracer activity 67. The graph 65 also includes the tracer activity 69 in the upper oesophagus area 29. Although not shown in graph 65, it is to be appreciated that linear regression or other curve fitting may be applied to the oesophageal data).

The summary also shows a summary of results during the second phase in the supine position as shown in graph 71. This includes the tracer activity 73 in the pharynx area 25 and a linear least squares fit line 74 of that tracer activity 73. The graph 71 also includes the tracer activity 75 in the upper oesophagus area.

The linear lines 68, 74 representing the tracer activity in the pharynx as well as the lines 69, 75 representing the upper oesophagus show trends in tracer activity that are indicative of reflux disease.

The summary also includes an indication 77 of the determined time to half clearance 60 of liquid content from the stomach (S HCT=12.42 minutes). Also provided is an indication of risk of pulmonary aspiration 79 which is based on the trend in tracer activity in the pharynx (such as an increasing trend when in the supine position).

FIGS. 11 and 12 illustrate CT images 81, SPECT images 83, and fused SPECT/CT images 85 that include details of anatomical features of the individual, including in the areas of interest. These can provide further detail of aspiration of the tracer and anatomical features that may be affected by refluxate.

FIG. 17 illustrates an output that includes: a graph 200 showing the frequency of tracer activity 205 above a specified threshold 205; and a graph 207 showing the oxygen saturation over the same time period. This allows a comparison 189, of the frequency of the trend in tracer activity and the oxygen saturation. This comparison 189 may, in some examples, also be performed by the computing device 7. In other examples, these graphs 200, 207 provide a visual representation so that an operator 13 can confirm the comparison 189 of the computing device 7.

Indicative Condition and Diagnosis (i) Gastro Oesophageal Reflux Disease (GORD)

The trends in the oesophagus 27 may be indicative of gastroesophageal reflux disease. This may cause distal complications (e.g. complications towards the oesophagus) that include metaplasia of the oesophageal lining and Barrett's oesophagus with the subsequent increased risk of carcinoma of the oesophagus.

In some examples, diagnosis includes determining the gradient of the detected activity 45, 69, 75 in the upper oesophagus 29. If the gradient is positive (which indicates an increase of tracer activity over time) this may be indicative that the oral dose of tracer (after initial swallowing of the dose through the oesophagus), is passing back upwards through the oesophagus. This may be illustrated, for example, by an initial decrease in tracer activity 45, 69 at the beginning of the first period (which represents swallowing or the time immediately after swallowing) followed by an increase in tracer activity (either at the later parts of the first period, or during the second and/or third periods).

This result and diagnosis may then be output to a display of the user interface 11 and may include an indication of the likelihood of severity of the condition based on the trend. For example, a percentage that is based on the gradient of detected activity 45, 69, 75.

Diagnosis may be assisted by reference to a look-up table based on validated data on the likelihood of aspiration of tracer into the lungs as a function of the gradients of the time-activity curves for the upper oesophagus and pharynx when upright and supine. So for example, rising time activity curves for the pharynx and upper oesophagus confer a 90% risk of lung aspiration while declining curves for both sites have a negative predictive value of 95% for lung aspiration of tracer.

(ii) Delayed Gastric Emptying

Delayed gastric emptying may also contribute to the frequency and severity of GORD. The analysis of gastric emptying of liquids may be achieved by analysing the curve 58, 58' that is based on detected activity of the stomach area 33. Metrics to determine delayed gastric emptying (if any) may be determined in different ways. In one example, the curve 58, 58' is used to determine 142 the time to half clearance 60 of the gastric liquid. This may include determining the time required to empty half of the oral dose (including the tracer) based on the curve 58, 58' and the maximum 59, 59' (e.g. when the stomach has the highest amount of the oral dose). This may then be compared to one or more benchmark times. In some example, the benchmark may be 16 minutes where the time for half clearance that is greater than 16 minutes is abnormal. It is to be appreciated that the benchmark may vary depending on characteristics of the individual (such as weight, height, sex, age, ethnicity, etc.).

In other examples, the activity 57 may be analysed in other ways to determine the rate of gastric emptying (for example, looking at the gradient of a line of best fit).

The result of the analysis, and diagnosis, may be output to a display (at the user interface 11) such as indication 77 in FIG. 10.

(iii) Laryngopharyngeal Reflux (LPR)

Trends in the pharynx 25 and other proximal areas may be indicative of potential proximal complications. This may include LPR with a heightened risk of carcinoma of the pharynx, lung aspiration and contamination of the sinuses and middle ear with risk of chronic infection.

In some examples, this includes analysing the tracer activity in the pharynx 67, 73 which may include analysing the linear least squares fit line 68, 74.

Referring to FIG. 10, the least squares fit line 68 during the initial upright position during the first period is declining. However, in the later supine position during the second period of tracer activity in the pharynx 25 has an ascending trend (as indicated by the positive gradient of line 74). This is indicative that initially (during the beginning of the first period) the oral dose has passed through the pharynx towards the stomach 33. However, in the later time periods (such as the second period and third period) at least some of the tracer from the oral dose is moving back towards the pharynx (i.e. reflux of the oral dose to the pharynx). The increase tracer activity is indicative of LPR and determination of such a condition, or risk of the condition, may be output 79 at the display.

In some examples, this may also increase the risk of pulmonary aspiration of the tracer. This may be determined as a percentage value based on trend in tracer activity in the pharynx. This is determined by a look-up table derived from the likelihood of aspiration of refluxate into the lungs based on the patterns of time activity curves for the pharynx and upper oesophagus when upright and supine.

Other qualities of laryngopharyngeal reflux may also be determined by the determined trends. This include determining if the reflux is intermittent (if the frequency of reflux above a specified threshold is relatively high) or continuous (if the frequency is relatively low, or is a single protracted event). Furthermore the severity of reflux may also be determined based on the amplitude and/or time of tracer activity 203 over the specified threshold 205.

(iv) Reflex Mediated Laryngopharyngeal Spasm

An indication of intermittent laryngopharyngeal reflux (based on a high frequency of tracer activity) in combination with a decreasing trend in oxygen saturation may be indicative of a reflex mediated laryngopharyngeal spasm. In some examples, the data for these trends are captured whilst the individual is in the supine position.

FIG. 17 shows a time period of tracer activity in the pharynx whilst the individual 3 is supine along with the oxygen saturation of the blood during the same time. This allows a determination of correlation of the frequency of reflux with the changes in oxygen saturation in real-time during the period of acquisition of the supine study (e.g. a 30 minute supine study during the second period). This is important information for the operator 13 to confirm the link of the frequency of reflux to the laryngopharynx with the fall in oxygen saturation. More importantly, it indicates that acid contact with the laryngopharynx or more certainly leads to some degree of spasm, with a resultant decrease in oxygen saturation. This information is important, as the reduction in oxygen saturation may also be due to the long-term effects of aspirated acid into the lungs which may lead to chronic reduction in resting oxygen saturation. This may also be an indicator of chronic lung disease.

In some examples, the comparison may include a visual comparison of these graphs 200, 207 by an operator. In other examples, the computer-implemented method performed by the computing device 7 performs the step of comparing 189 the frequency of the trend in tracer activity (that is above a specified threshold or at a specified threshold) with the trend in oxygen saturation. The computing device 7 may then provide an output of an indication of reflex mediated laryngopharyngeal spasm. This output may be a probability value, or a binary indication, based on the correlation of a relatively high frequency of tracer activity combined with a decrease in oxygen saturation.

(v) Aspiration to Other Areas and Overlay With SPECT/CT

The present disclosure may also assist determining the impact and severity of reflux in areas of interest in the individual. In one example, the scanner 5 is a SPECT/CT scanner that can provide images of tracer activity at respective areas of interest. Referring to FIG. 11, this may include tracer activity images (from SPECT) 83 at respective areas of interest that is overlayed with CT images 81 to generate 160 fused SPECT/CT images 85.

Importantly, this allows the operator 13 to identify areas of interest that has tracer activity, which may correspond to areas that may be affected by refluxate. Such areas of interest may include nasal turbinates, the maxillary sinuses, Eustachian tube and/or the middle ears.

For example with reference to FIG. 11, tracer activity in the nasopharynx 91 (in images 83) is overlayed with the corresponding CT images 81 such that the tracer and the respective anatomical feature affected can be identified in fused image 85.

Furthermore, tracer activity can be seen in the right Eustachian tube 93, right maxillary sinus 95 and nasal turbinates 97 as illustrated in FIG. 12.

Figure 13B:
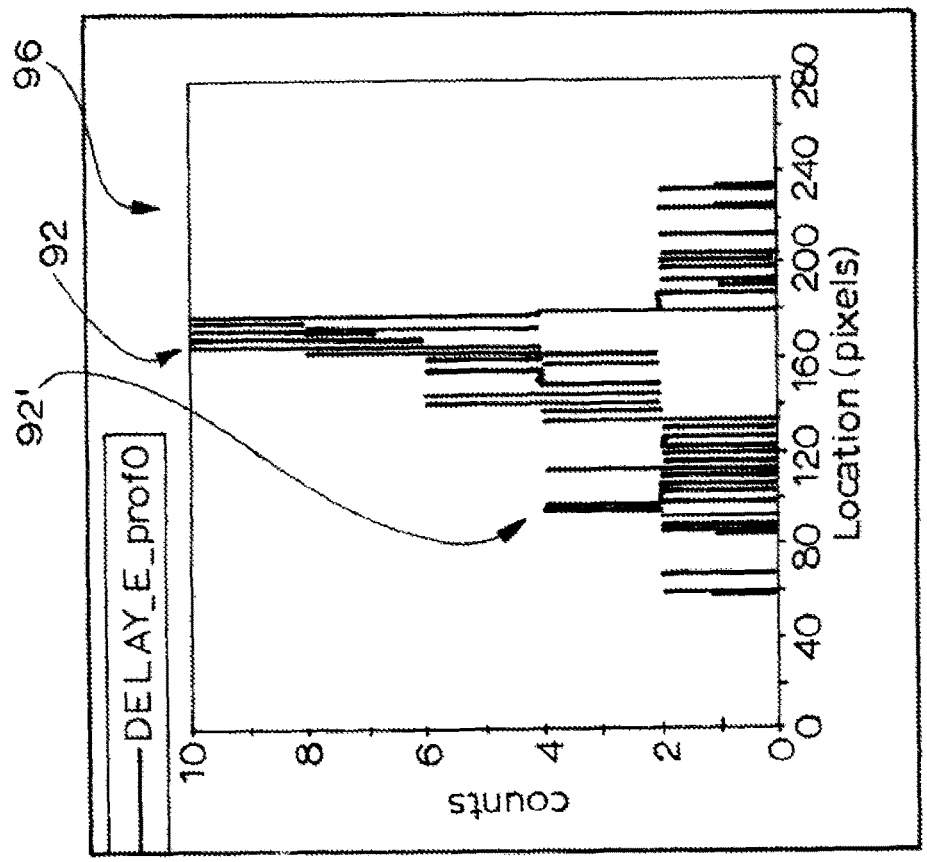
FIG. 13B is a line profile showing count densities in a portion of the image in FIG. 13A.
Figure 13A:
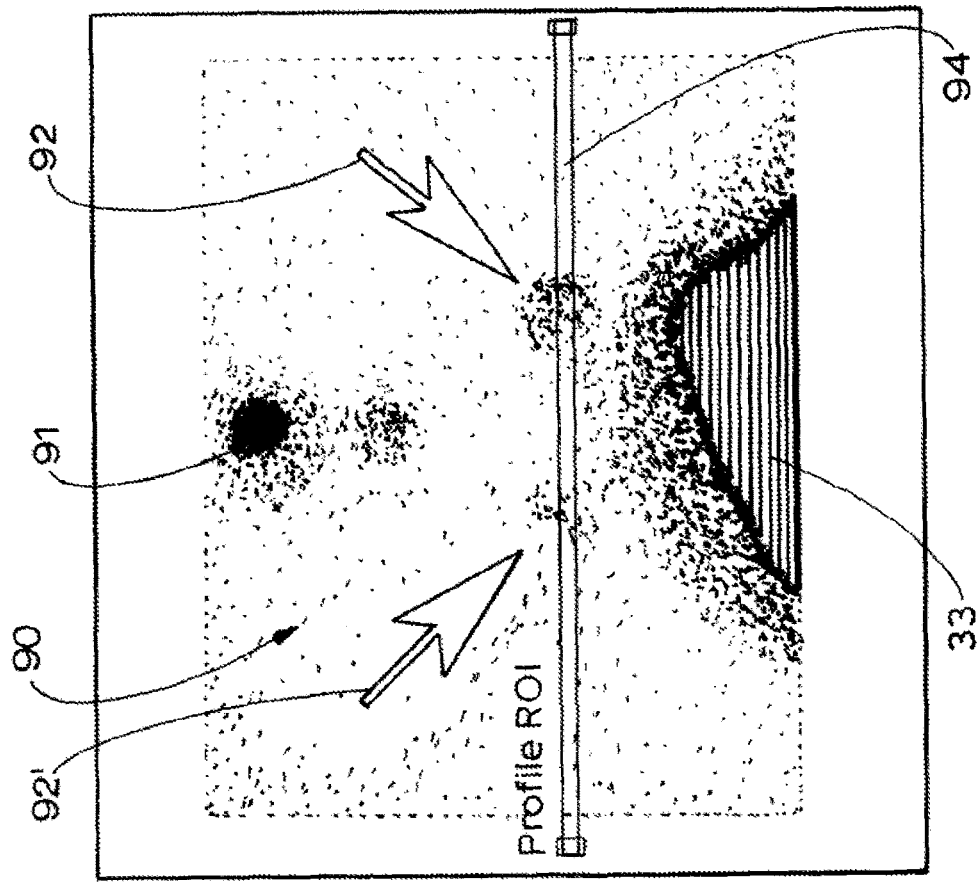
FIG. 13A is an example representation of a SPECT image that shows aspiration in at least part of the lung.

FIG. 13A shows a SPECT image 90 of tracer activity in the lower head, neck and upper torso. In this example, the image 90 was generated from data in the third period (e.g. the delayed phase of the study). This illustrates tracer activity in the nasopharynx 91 as well as to stomach 33. In addition, there is tracer activity in parts of the lung as indicated by arrows 92, 92'. This is indicative of aspiration of the tracer in both lungs. A line profile 96 along the line 94 in FIG. 13A is illustrated in FIG. 13B. This illustrates count densities along the line 94, including relatively higher counts that correspond to the lung location indicated by arrows 92, 92'.

Therefore the fused SPECT/CT images provide clear indication of refluxate in the areas of interest to diagnose reflux to these areas of interest. In some examples, these SPECT/CT images are provided on a display of the user interface 11. It is to be appreciated that this output (and other diagnosis outputs described above) may also be output onto physical medium (such as printing a hard copy or a soft copy to a data storage medium) and/or sent to one or more other computing devices via a network.

The Relationship Between the Patterns of Time Activity Curves for the Pharynx and Upper Oesophagus and Lung Aspiration of Tracer in the Scintigraphic Reflux Studies Data from over 750 documented cases of gastro-oesophageal reflux to the level of the pharynx was correlated evidence of lung aspiration of tracer in the delayed images.

A significant difference for lung aspiration was found between intermittent full column gastro-oesophageal reflux and continuous gastro-oesophageal reflux. Continuous gastro-oesophageal reflux was associated with lung aspiration in 51% of patients. The curves were relatively non-predictive for aspiration in this group, as even declining time activity curves are associated with lung aspiration of tracer. However, in the group with intermittent full column gastro-oesophageal reflux, the predictive value of the time activity curves was significantly helpful in establishing the probability of lung aspiration of refluxate. In patients with a rising time activity curve for the pharynx and upper oesophagus in the upright and supine position, the positive predictive value for lung aspiration of refluxate was 85%. The negative predictive value of declining time activity curves for the pharynx and upper oesophagus was 95%, except in cases of continuous full column gastro-oesophageal reflux. In cases where a flat or declining time activity curve for the pharynx in the upright position was found together with a rising time activity curve for the supine position, the positive predictive value for lung aspiration of refluxate was 76%.

Additional Examples of Results

FIGS. 18A to 19C illustrate another example of results from the method 100' performed by the system 1.

Figure 18A:
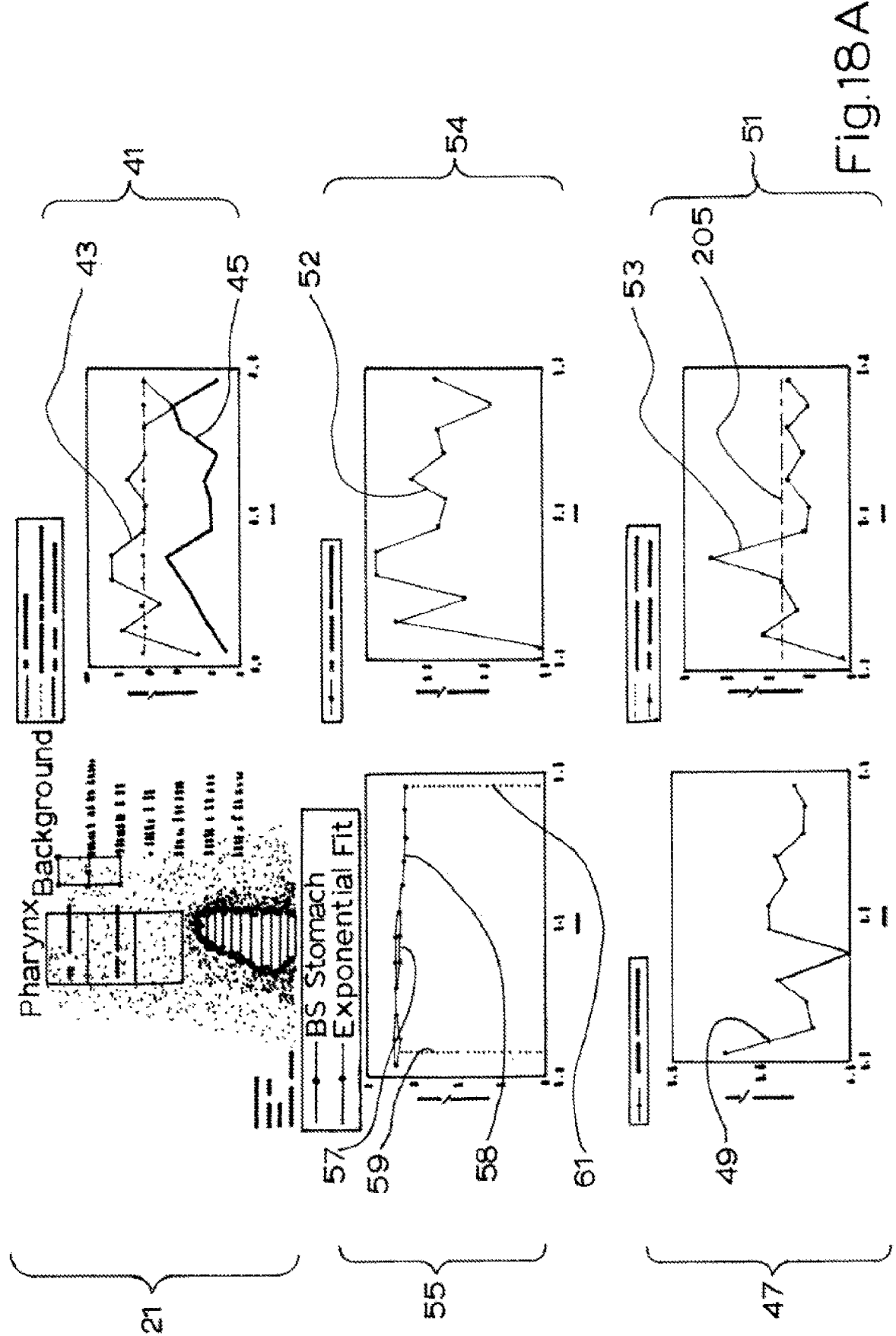
FIG. 18A is a graphical representation data captured during a first period with an individual in the upright position in accordance with another example.
Figure 18B:
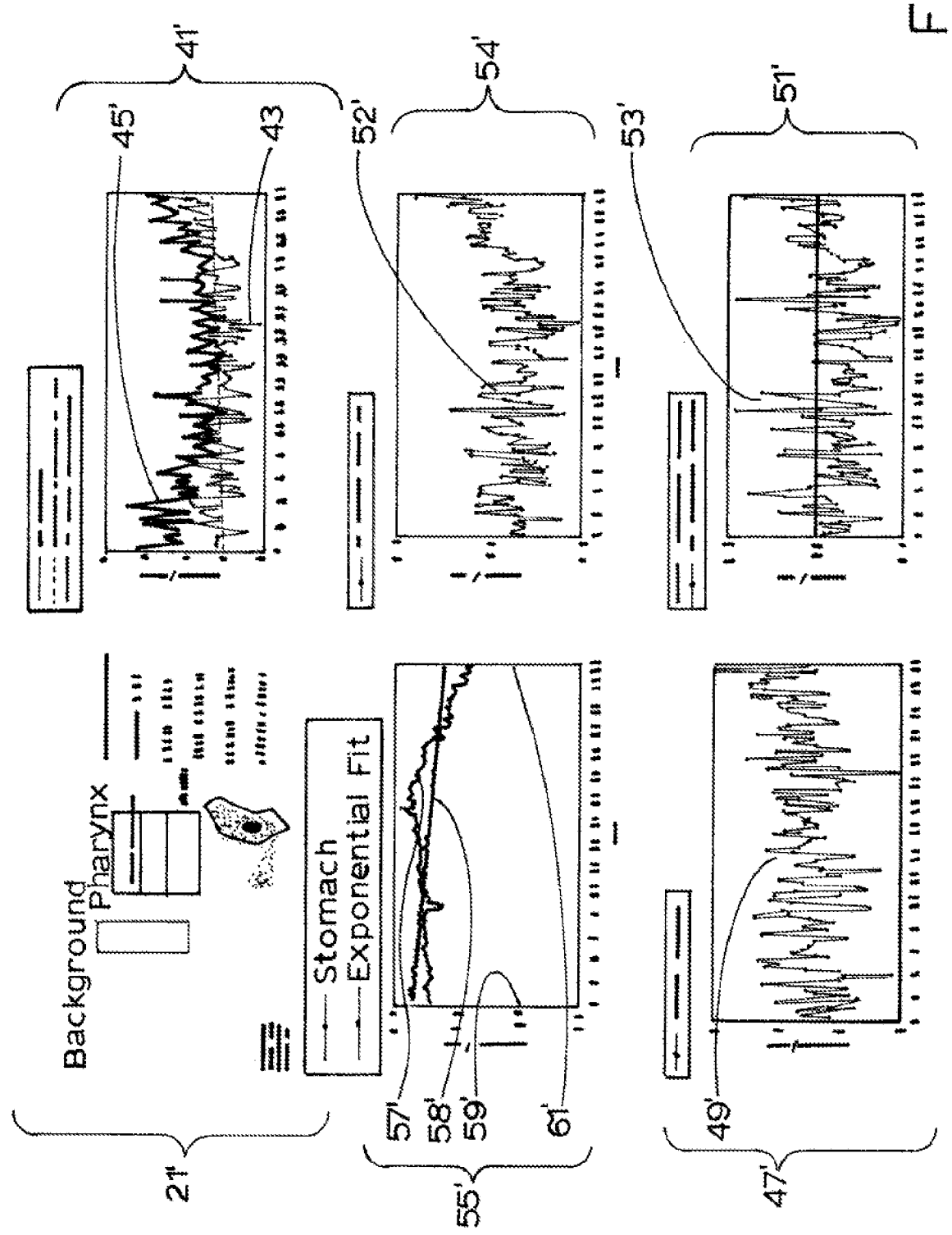
FIG. 18B is graphical representation of data captured during a second period with the individual in the supine position in accordance with the example of FIG. 18A.

FIG. 18A is a graphical representation data captured during a first period with an individual in the upright position. FIG. 18B is graphical representation of data captured during a second period with the individual in the supine position. The labels in the earlier example in FIGS. 7 and 8 are applicable to these graphical representations.

Figure 19A:
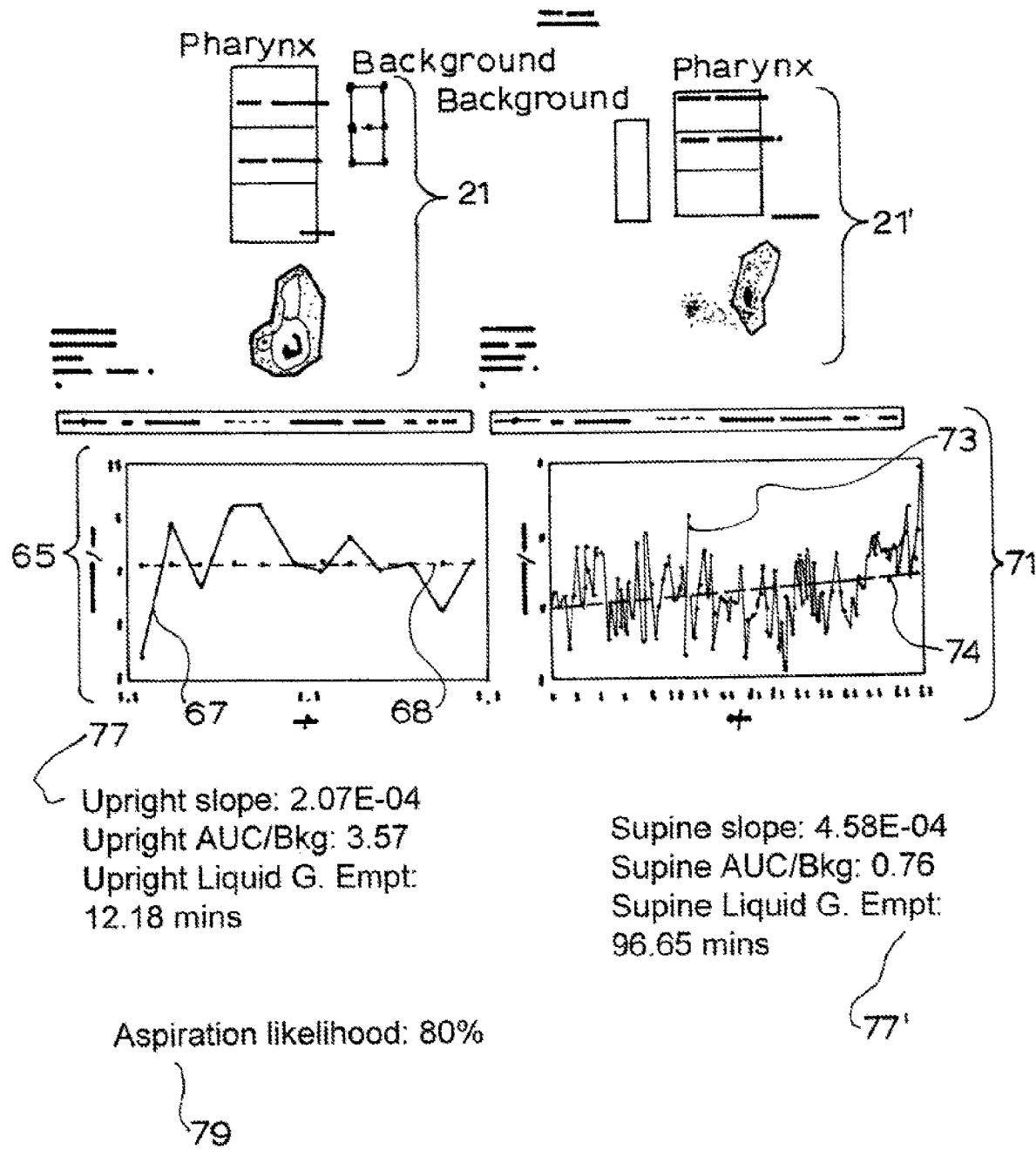
FIG. 19A is an example representation of a summary of the upright and supine data captured by the system in accordance with the example of FIGS. 18A and 18B.

FIG. 19A illustrates an example representation of a summary of upright and supine data, where the upright data is on the left hand side and the supine data is on the right hand side. The image frames 21, 21' show tracer activity in the upright and supine positions. The graphs 65 and 71 are similar to the example in FIG. 10 above, but showing tracer activity from the pharynx only during the first period (with the individual in the upright position) and second period (with the individual in the supine position). An indication 77, 77' of the time to half clearance of liquid content from the stomach is also provided for the upright and supine positions.

An indication 79 of the likelihood of aspiration is also provided, which in this case is 80%.

Figure 19C:
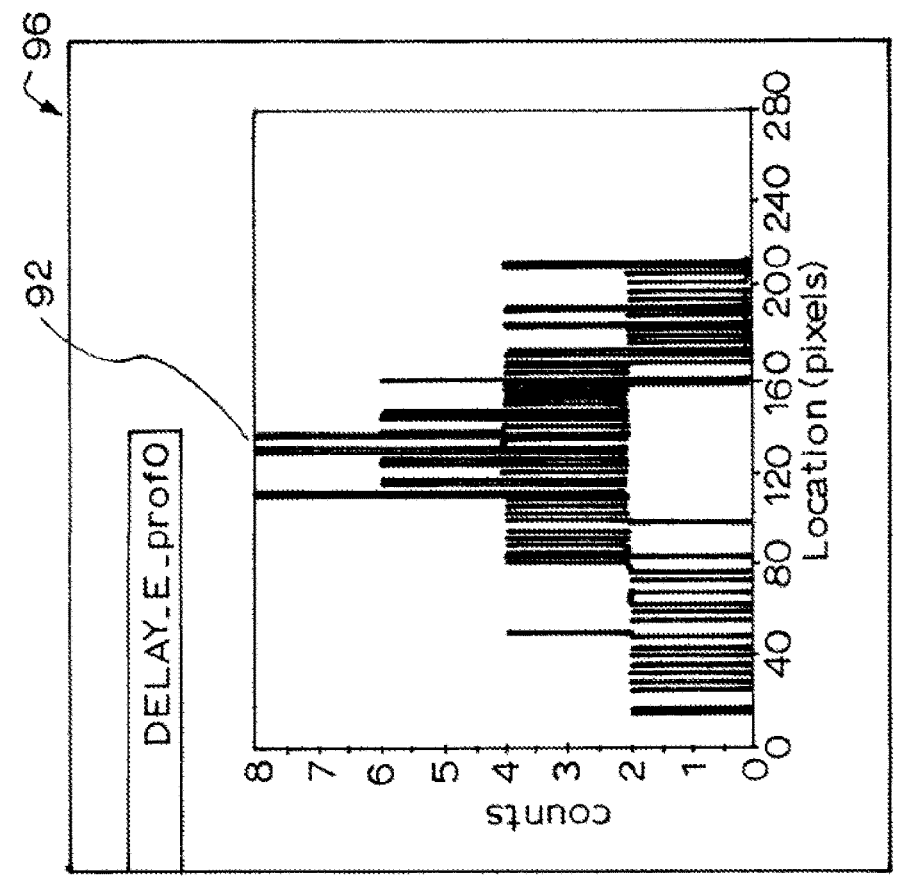
FIG. 19C is a line profile showing count densities in a portion of the image in FIG. 19B.
Figure 19B:
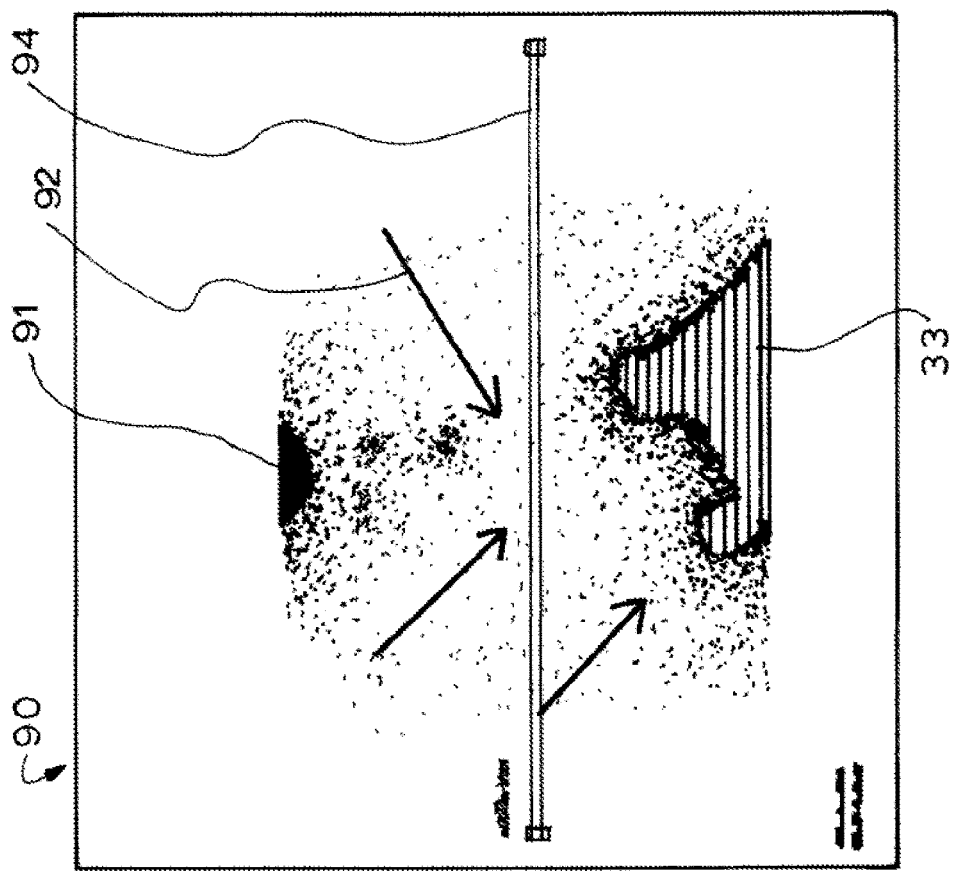
FIG. 19B is an example representation of a SPECT image that shows aspiration in at least part of the lung in accordance with the examples in FIGS. 18A and 18B.

FIG. 19B shows a SPECT image 90 of tracer activity in the lower head, neck and upper torso. This illustrates tracer activity in the nasopharynx 91 as well as to stomach 33. In addition, there is tracer activity in parts of the lung as indicated by arrow 92. This is indicative of aspiration of the tracer in the lungs. A line profile 96 along the line 94 in FIG. 19B is illustrated in FIG. 19C. This illustrates count densities along the line 94, including relatively higher counts that correspond to the aspiration in the lungs as indicated by arrow 92.

Figure 20A:
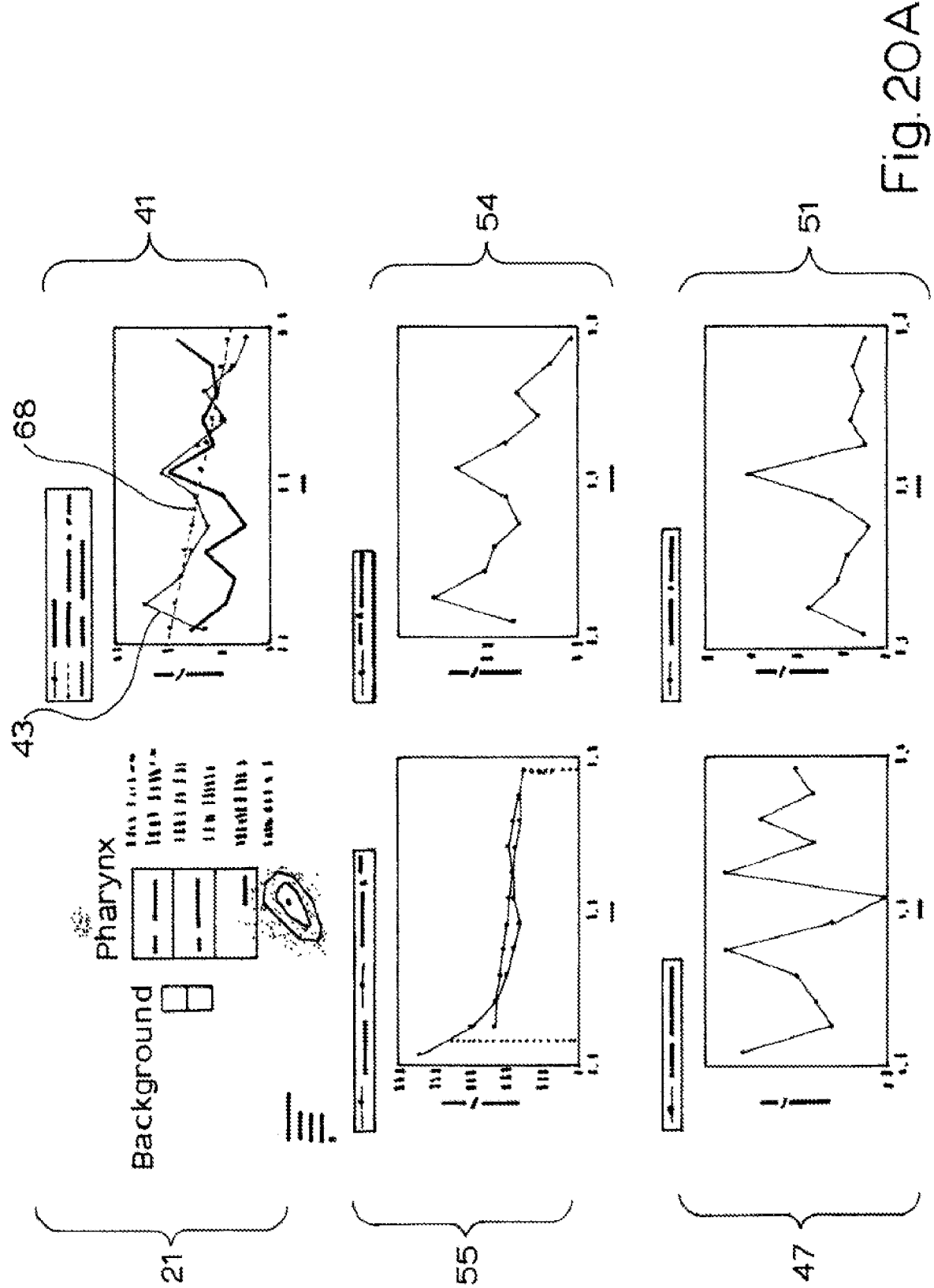
FIG. 20A is a graphical representation data captured during a first period with an individual in the upright position in position where there is a falling curve of tracer activity in the pharynx.
Figure 20B:
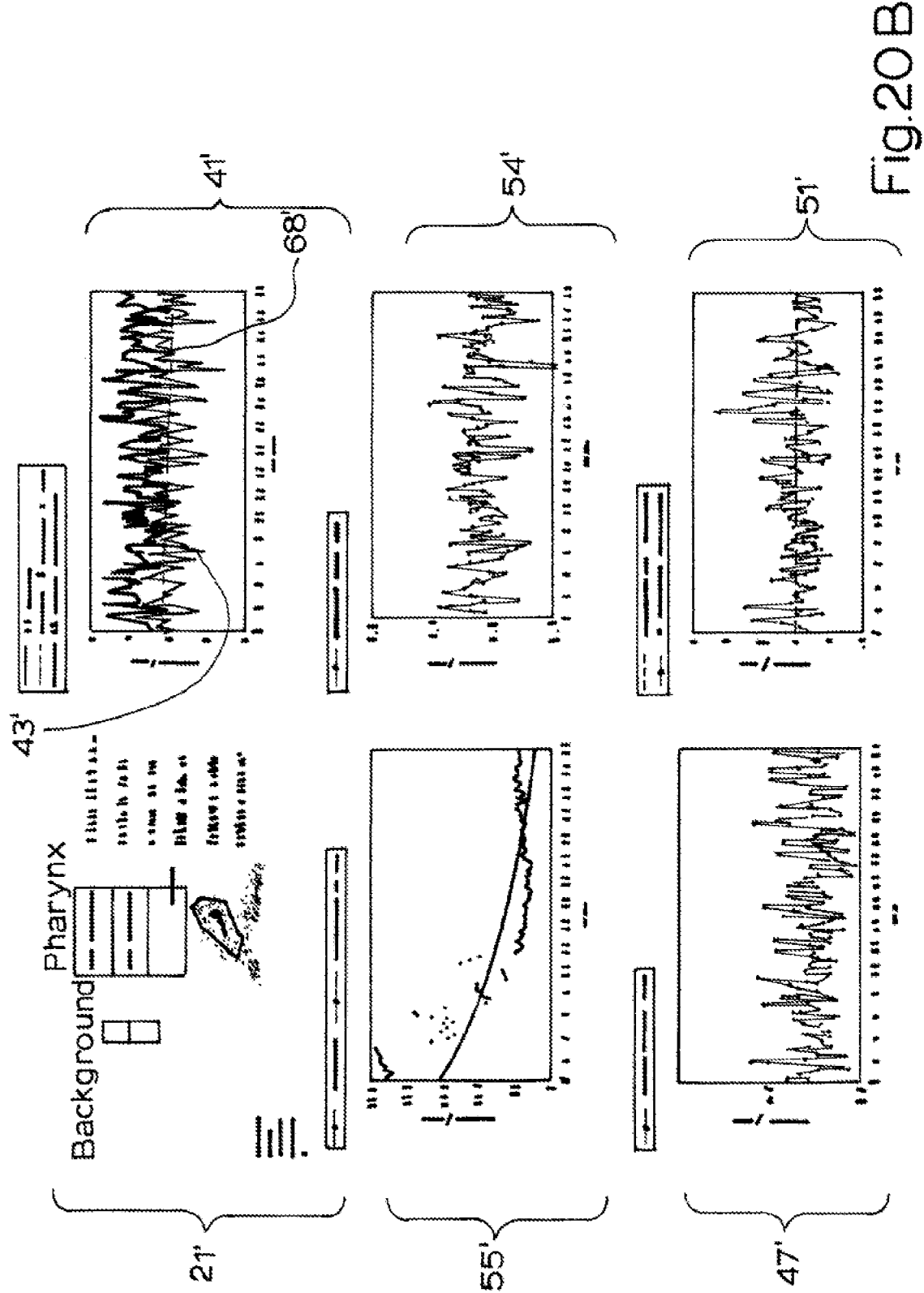
FIG. 20B is graphical representation of data captured during a second period, following the first period in FIG. 20A, with the individual in the supine position where there is a falling curve of tracer activity in the pharynx.

Another example study is shown in FIGS. 20A and 20B. FIG. 20A is a graphical representation data captured during a first period with an individual in the upright position. FIG. 20B is graphical representation of data captured during a second period with the individual in the supine position. As shown in graphs 41 and 41', the tracer activity 43, 43' in the pharynx is falling in both the upright and supine positions. This indicates that there is a rapid clearance of tracer from the pharynx back into the oesophagus and the stomach, significantly reducing the risk of contamination of the laryngopharynx and lungs.

Figure 21A:
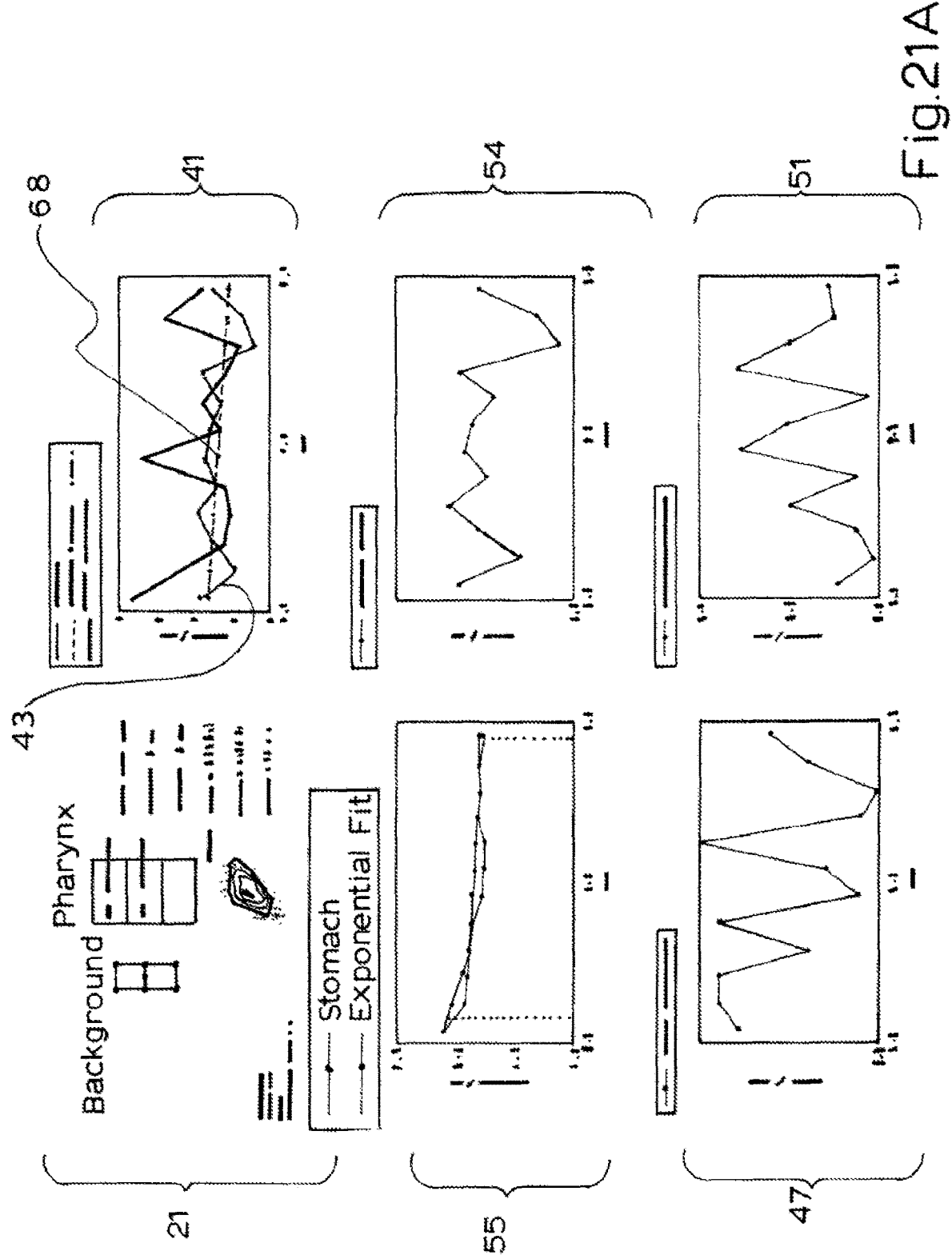
FIG. 21A is a graphical representation data captured during a first period with an individual in the upright position where there is a falling curve of tracer activity in the pharynx.
Figure 21B:
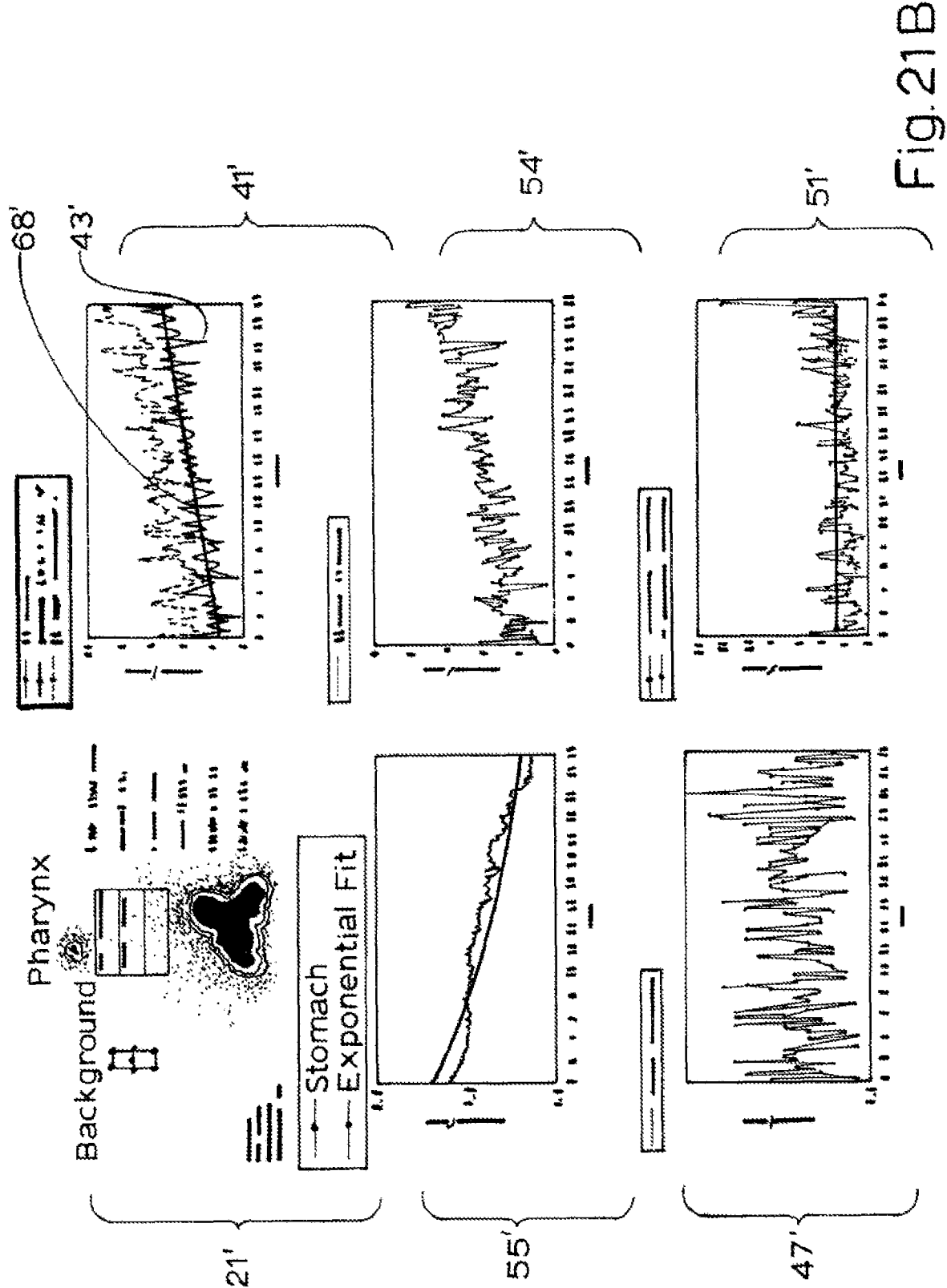
FIG. 21B is graphical representation of data captured during a second period, following the first period in FIG. 21A, with the individual in the supine position where there is a rising curve of tracer activity in the pharynx.

Another example study is shown in FIGS. 21A and 21B. FIG. 21A is a graphical representation data captured during a first period with an individual in the upright position. FIG. 21B is graphical representation of data captured during a second period with the individual in the supine position. A falling curve 43, 68 for the pharynx when upright (as shown in graph 41 in FIG. 21A, indicates that there is good gravitational clearance of tracer from the pharynx, reducing the risk of contamination of the laryngopharynx or lungs when upright. The rising curve 43', 68' in the supine position, as shown in graph 41' FIG. 21B, indicates that in the absence of gravity, the pharynx is failing to clear reflux to fluid, thereby increasing the risk of laryngopharyngeal and lung contamination.

Figure 22A:
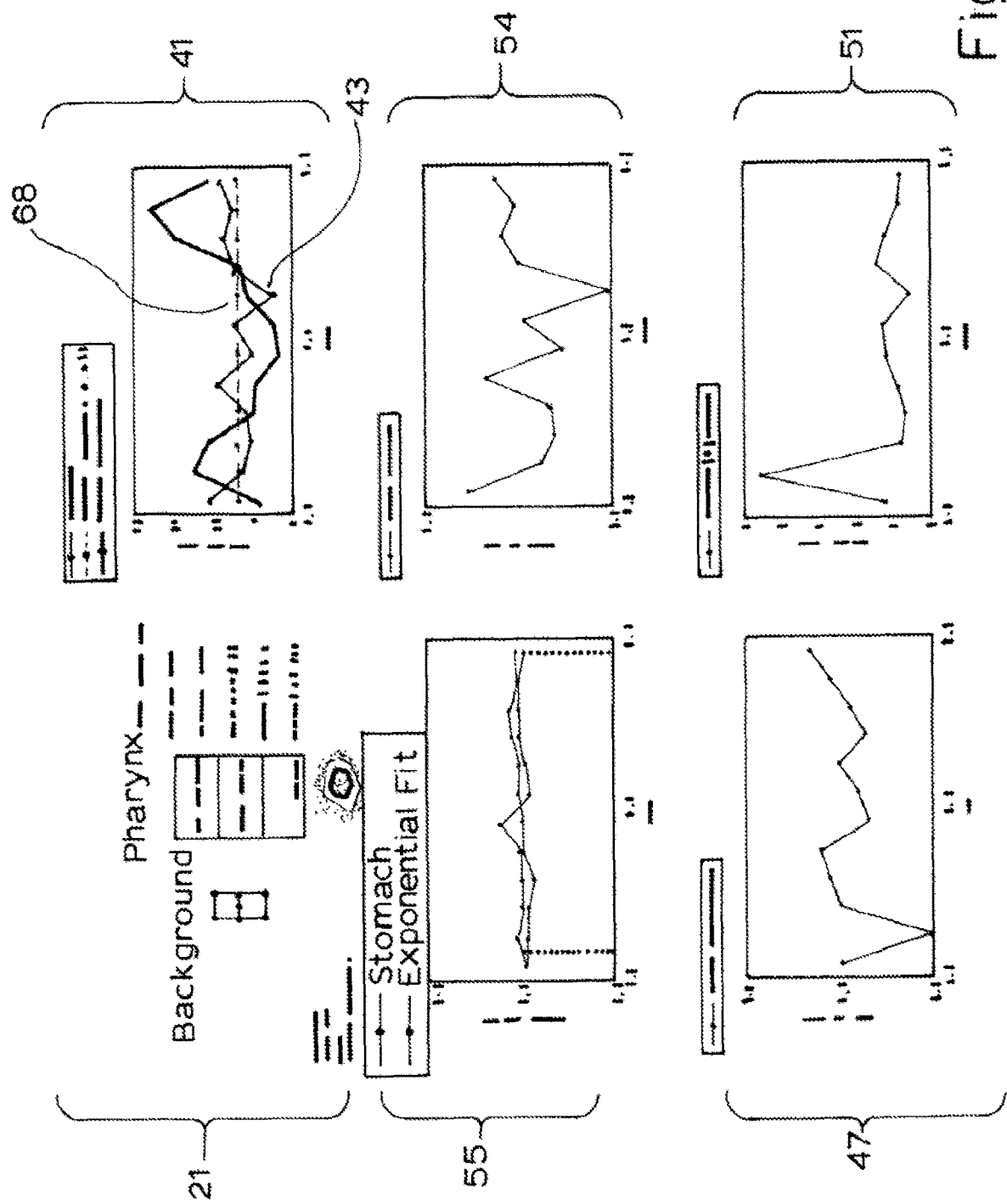
FIG. 22A is a graphical representation data captured during a first period with an individual in the upright position where there is a flat curve of tracer activity in the pharynx.
Figure 22B:
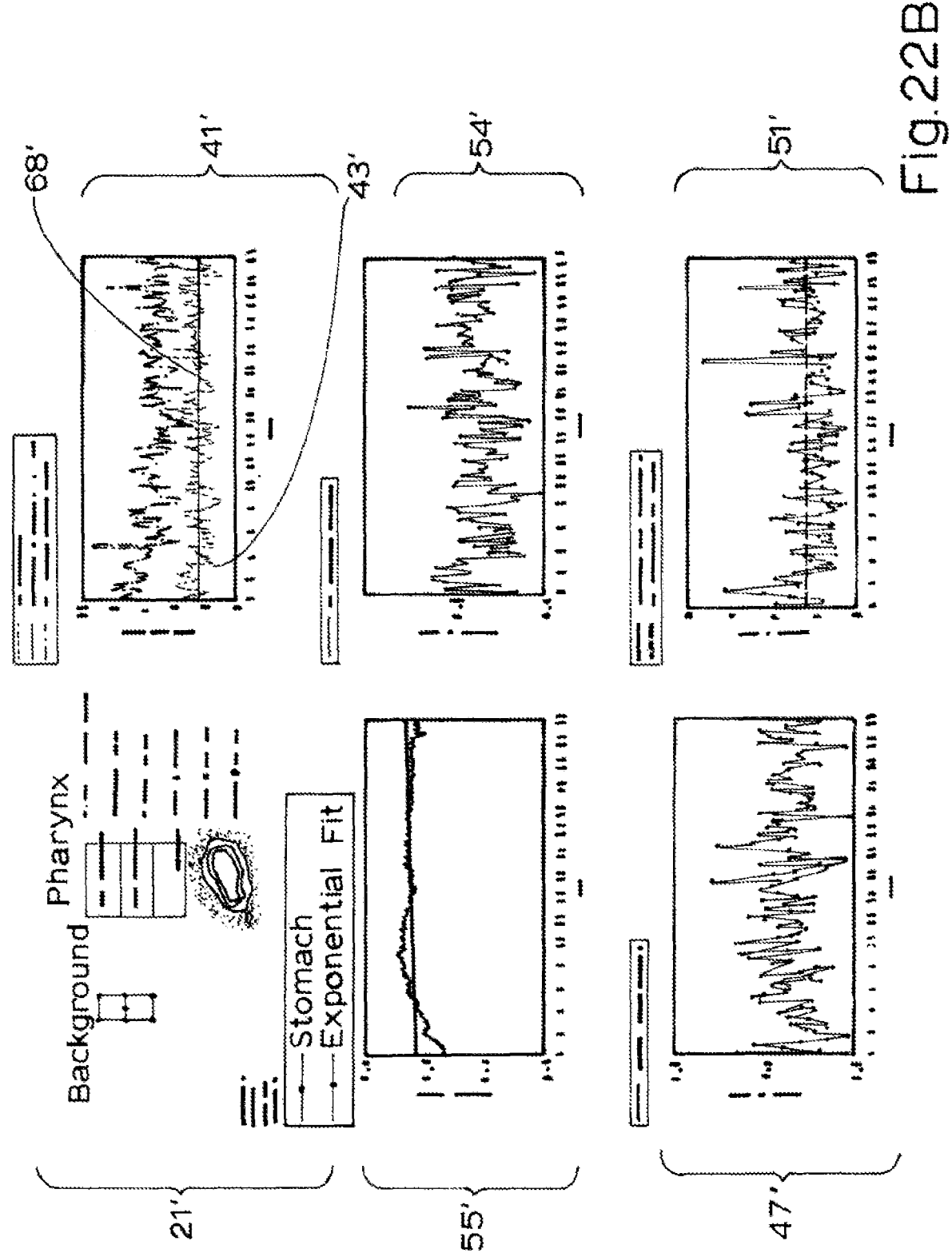
FIG. 22B is graphical representation of data captured during a second period, following the first period in FIG. 22A, with the individual in the supine position where there is a flat curve of tracer activity in the pharynx.

Another example study is shown in FIGS. 22A and 22B. FIG. 22A is a graphical representation data captured during a first period with an individual in the upright position. FIG. 22B is graphical representation of data captured during a second period with the individual in the supine position. Flat curves 43, 43', 68, 68' for the pharynx in the upright and supine position (as shown in graphs 41, 41' in FIGS. 22A and 22B) indicates a balanced pattern of clearance for fluid that is both coming up to the pharynx from the oesophagus and being cleared down the oesophagus back into the stomach. This would carry an intermediate risk of contamination of the laryngopharynx and lungs by the refluxed liquid.

Processing Device

Figure 14:
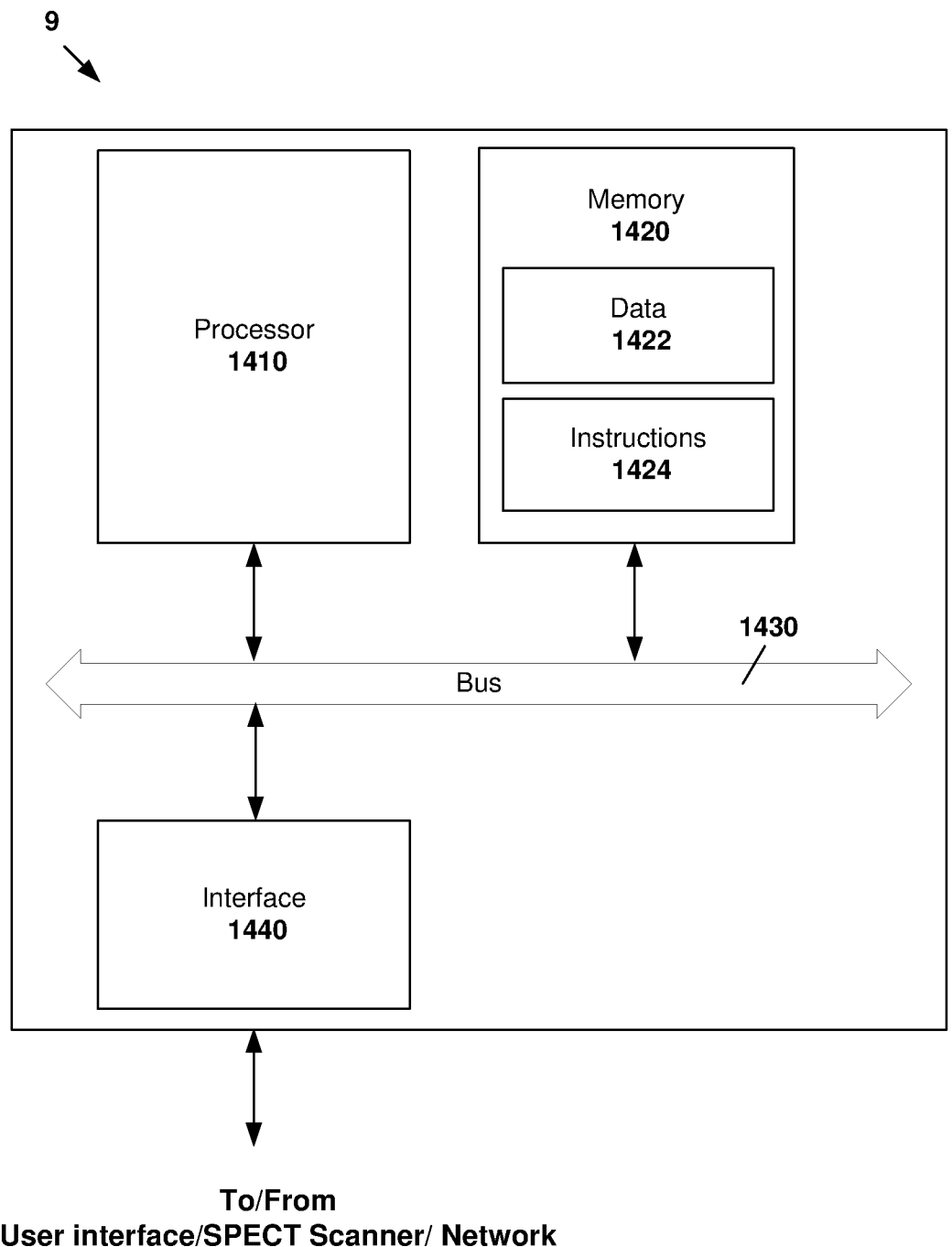
FIG. 14 illustrates a schematic of an example processing device.

FIG. 14 illustrates an example of a processing device 9 that may be provided in the computing device 7. The processing device 9 includes a processor 1310, a memory 1320 and an interface device 1340 that communicate with each other via a bus 1330. It is to be appreciated that the interface 1340 may be one or more interfaces. The memory 1320 may store instructions 1324 and data 1322 for implementing steps in the method 100 described above, and the processor 1310 performs the instructions from the memory 1320 to implement the steps in the method 100. The interface device 1340 facilitates communication with the communications network 213 and, in some examples, with a user interface 11 and other peripherals (such as the SPECT scanner 5). In some examples, the interface 1340 also facilitates communication to other processing devices 9.

The processing device 9 may further be implemented within a cloud computing environment, such as a managed group of interconnected servers hosting a dynamic number of virtual machines.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for diagnosing a reflux disease in an individual, the method comprising:
(A) administering a single oral dose of tracer in 75 mL to 200 ml of water to the individual, wherein the tracer includes technetium phytates in the range of 60 to 100 MBq;
(B) capturing, with a single photon emission computed tomography (SPECT) scanner, data representative of multiple image frames of the individual in areas of interest, wherein multiple image frames of the area of interest includes the oesophagus, and the pharynx/laryngopharynx, wherein the data representative of multiple image frames are captured over time after administration of the single oral dose of tracer;
(C) determining one or more trend(s) in tracer activity over time in the areas of interest based on the data representative of multiple image frames in the areas of interest over time, wherein each image frame has a sampling time of greater than 5 seconds and less than or equal to 60 seconds, wherein the trend(s) in tracer activity over time is indicative of the reflux disease,
wherein at least part of the data representative of multiple image frames are captured over a first time period with the individual in an upright position, wherein the first time period is in a range between
administration of the single oral dose and 30 minutes after; and
wherein at least part of the data representative of multiple image frames are captured over a subsequent time period that occurs between 90 minutes to 150 minutes after administration of the single oral dose and with the individual in a supine position; and
(D) diagnosing the reflux disease based on the trend(s) in tracer activity over time.

2. The method according to claim 1 further comprising determining a frequency of the trend in tracer activity in the pharynx that is above a specified threshold or in a specified range, wherein a frequency of tracer activity that crosses the specified threshold multiple times is indicative of intermittent laryngopharyngeal reflux and a single protracted occurrence above the threshold is indicative of continuous laryngopharyngeal reflux, and wherein a frequency indicative of intermittent laryngopharyngeal reflux is indicative of an increased probability of lung aspiration of refluxate.

3. The method according to claim 2 further comprising:
capturing, with an oxygen saturation sensor, an oxygen saturation of the blood of the individual over time, wherein a decreasing trend in oxygen saturation and an indication of intermittent laryngopharyngeal reflux are indicative of spasm of the laryngopharynx due to reflux or aspiration of the refluxed gastric fluid into the lungs.

4. The method according to claim 1 further comprising determining an amplitude and/or time of the trend in tracer activity in the pharynx that is above a second specified threshold, wherein the amplitude and/or time is indicative of a severity of laryngopharyngeal reflux.

5. The method according to claim 1 wherein an ascending or flat trend in tracer activity over time in the oesophagus is indicative of the tracer in the oesophagus and significant gastroesophageal reflux, and wherein an ascending trend in tracer activity over time in the pharynx is indicative of aspiration of the tracer and laryngopharyngeal reflux.

6. The method according to claim 1 wherein at least part of the data representative of multiple image frames are captured over another subsequent time period after the first time period that occurs up to 30 minutes after administration of the single oral dose and with the individual in the supine position.

7. The method according to claim 1 wherein the sampling time for each image frame is in the range of 15 to 30 seconds.

8. The method according to claim 1 wherein the areas of interest includes the stomach of the individual, wherein the method further comprises:
determining a trend in tracer activity by exponential fit of tracer activity in the stomach over time; and
determining a time to half clearance of gastric liquid based on the exponential fit of tracer activity,
wherein a time to half clearance greater than 16 minutes is indicative of an individual as having a prolonged liquid gastric emptying.

9. The method according to claim 1 wherein the SPECT scanner is a SPECT/CT scanner that further includes x-ray computed tomography (CT) to provide data representative of multiple image frames of the individual that includes details of anatomical features of the individual.

10. The method according to claim 1 wherein the area of interest that includes the oesophagus includes the upper oesophagus and the lower oesophagus, and the method further includes determining, for the upper oesophagus and lower oesophagus, the respective trend in tracer activity by least squares fit or linear regression of tracer activity over time.

11. A system for diagnosing a reflux disease in an individual, the system comprising:
a single photon emission computed tomography (SPECT) scanner, wherein the SPECT scanner is configured to capture data representative of multiple image frames in areas of interest that include the: (i) oesophagus, and (ii) the pharynx/laryngopharynx of the individual, wherein the SPECT scanner is further configured to capture data representative of multiple image frames of the individual in a supine position and an upright position; and
a processing device configured to:
receive, from the SPECT scanner, data representative of multiple image frames of a single dose orally administered tracer in 75 mL to 200 ml of water in areas of interest that include the pharynx/laryngopharynx and oesophagus, wherein the data representative of multiple image frames of the tracer are captured over time in the areas of interest after administration of the tracer;
determine one or more trend(s) in tracer activity over time in the areas of interest based on the multiple image frames in the areas of interest over time, wherein each image frame has a sampling time of greater than 5 seconds and less than or equal to 60 seconds, wherein the trend(s) in tracer activity over time is indicative of the reflux disease, wherein the tracer includes technetium phytates in the range of 60 to 100 MBq,
wherein at least part of the data representative of multiple image frames are captured over a first time period with the individual in an upright position, wherein the first time period is in a range between administration of the oral single dose orally administered tracer and 30 minutes after; and
wherein at least part of the data representative of multiple image frames are captured over a subsequent time period that occurs between 90 minutes to 150 minutes after administration of the single dose orally administered tracer and with the individual in a supine position.

12. The system according to claim 11 wherein the processing device is further configured to:
determine, separately, the tracer activity in each of the areas of interest including the pharynx/laryngopharynx and the oesophagus; and
determine, for each area of interest, the trend in tracer activity by linear regression of tracer activity over time.

13. The system according to claim 11 wherein the processing device is further configured to:
determine, separately, the tracer activity in the upper oesophagus and the lower oesophagus; and
determine, for the upper oesophagus and the lower oesophagus, the respective trend in tracer activity by least squares fit or linear regression of tracer activity over time.

14. The system according to claim 11 wherein the SPECT scanner further captures data representative of image frames of a background area, wherein the background area is outside a fluid path of the nasopharynx, larynx, and oesophagus, wherein the processing device is further configured to:
determine background radiation based on activity in the background area; and
enhance the data representative of the multiple images by factoring the background radiation.

15. The system according to claim 11 wherein the areas of interest includes the nasal turbinates, maxillary sinuses, Eustachian tube and/or the middle ears, wherein the processing device is further configured to:
generate, at a display, one or more representations of the tracer activity at the nasal turbinates, maxillary sinuses, Eustachian tube and/or the middle ears,
wherein the tracer activity at the nasal turbinates, maxillary sinuses, Eustachian tube and/or middle ears is indicative of aspiration of the tracer.

16. The system according to claim 11, wherein the processing device is further configured to:
generate, at a display, one or more representations of the one or more trend(s) in tracer activity over time.

17. The system according to claim 11, wherein at least part of the data representative of multiple image frames are captured over another subsequent time period after the first time period that occurs up to 30 minutes after administration of the single dose orally administered tracer and with the individual in the supine position.

18. A computer-implemented method for diagnosing a reflux disease in an individual, wherein the individual is administered a single oral dose of tracer in 75 mL to 200 ml of water, the method comprising:
receiving, from a single photon emission computed tomography (SPECT) scanner, data representative of multiple image frames of the orally administered tracer in the individual in areas of interest, wherein the multiple image frames of the area of interest includes at least (i) the oesophagus, and (ii) pharynx/laryngopharynx, wherein the data representative of multiple image frames are captured over time after administration of the single oral dose of tracer;
determining one or more trend(s) in tracer activity over time in the areas of interest based on the multiple image frames of the areas of interest over time, wherein each image frame has a sampling time of greater than 5 seconds and less than or equal to 60 seconds, wherein the trend(s) in tracer activity over time is indicative of the reflux disease, wherein the tracer includes technetium phytates in the range of 60 to 100 MBq,
wherein at least part of the data representative of multiple image frames are captured over a first time period with the individual in an upright position, wherein the first time period is in a range between administration of the single oral dose of tracer and 30 minutes after; and wherein at least part of the data representative of multiple image frames are captured over a subsequent period that occurs between 90 minutes to 150 minutes after administration of the single oral dose of tracer and with the individual in a supine position.

* * * * *